United States Patent [19]

Alexander-Bridges et al.

[11] Patent Number: 5,496,831
[45] Date of Patent: Mar. 5, 1996

[54] INHIBITION OF INSULIN-INDUCED ADIPOSIS

[75] Inventors: Maria C. Alexander-Bridges, Newtonville; Hui-Fen Zhao, Brookline, both of Mass.

[73] Assignee: The General Hospital Corporation, Boston, Mass.

[21] Appl. No.: 242,409

[22] Filed: May 13, 1994

[51] Int. Cl.$^6$ .................................................. A01N 43/42
[52] U.S. Cl. ........................................... 514/290; 514/294
[58] Field of Search .................................... 514/290, 294

[56] References Cited

U.S. PATENT DOCUMENTS

| | | | |
|---|---|---|---|
| 5,247,076 | 9/1993 | Goulet et al. | 540/456 |
| 5,252,732 | 10/1993 | Sinclair et al. | 540/456 |
| 5,258,389 | 11/1993 | Goulet et al. | 514/291 |

FOREIGN PATENT DOCUMENTS

| | | |
|---|---|---|
| 0507555 | 10/1992 | European Pat. Off. |
| WO92/00313 | 1/1992 | WIPO. |
| WO93/16083 | 8/1993 | WIPO. |

OTHER PUBLICATIONS

Agras, Chapter III, Scientific American, Rubenstein et al., (eds.) New York, 1978, pp. 1–14.
Albers et al., FKPB–Rapamycin Inhibits a Cyclin–dependent Kinase Activity and a Cyclin D1–Cdk Association in Early G1 of an Osteosarcoma Cell Line, J. Biol. Chem. 268:22825–22829, 1993.
Alexander et al., Insulin Regulation of Protein Biosynthesis in Differentiated 3T3 Adipocytes, J. Biol. Chem. 260:11978–11985, 1985.
Alexander, et al., Tissue Specific Regulation of the Glyceraldehyde–3–phosphate Dehydrogenase Gene by . . . of 3T3 Adipocytes, UCLA Symposia on Molecular and Cellular Biology (New York: Liss, Inc), pp. 247–261, 1990.
Alexander et al., Insulin Stimulates Glyceraldehyde–3–phosphate Dehydrogenase Gene Expression Through Cis–acting DNA Sequences, Proc. Natl. Acad. Sci. USA 85:5092–5096, 1988.
Arroyo and Raychaudhuri, Retinoblastoma–repression of E2F–dependent Transcription Depends on the Ability of . . . with E2F and is Abrogated by the Adenovirus E1A Oncoprotein, Nucleic Acids Research 20:5947–5954, 1992.
Bagchi et al., The Retinoblastoma Protein Copurifies with E2F–1, an E1A–Regulated Inhibitor of the Transcription Factor E2F, Cell 65:1063–1072, 1991.
Cherington, Rapamycin Suppression of Murine Adipocyte Differentiation: Okadaic Acid Counteracts a Subset of Rapamycin . . . Differentiation–Dependent Events, J. Cell. Biochem. Suppl. 0 (18 Part A) 1994, p. 160.
Bandara et al, Adenovirus E1a Prevents the Retinoblastoma Gene Product from Complexing with a Cellular Transcription Factor, Nature 351:494–497, 1991.
Berger et al., Decreased Expression of the Insulin–responsive Glucose Transporter in Diabetes and Fasting, Nature 340:70–72, 1989.

Cao et al., Independent Binding of the Retinoblastoma Protein and p107 to the Transcription Factor E2F, Nature 355:176–179, 1992.
Cao et al., Identification and Characterization of the Egr–1 Gene Product, a DNA–Binding Zinc Finger Protein Induced by Differentiation and Growth Signals, Mol. Cell. Biol. 10:1931–1939, 1990.
Charron and Kahn, Divergent Molecular Mechanisms for Insulin–resistant Glucose Transport in Muscle and Adipose Cells in Vivo, J. Biol. Chem. 265:7994–8000, 1990.
Chellappan et al., Adenovirus E1A, Simian Virus 40 Tumor Antigen, and Human Papillomavirus E7 Protein Share . . . Factor E2F and the Retinoblastoma Gene Product, Proc. Natl. Acad. Sci. USA 89:4549–4553, 1992.
Chellappan et al., The E2F Transcription Factor is a Cellular Target for the RB Protein, Cell 65:1053–1061, 1991.
Chittenden et al., The T/E1A–Binding Domain of the Retinoblastoma Product can Interact Selectively with a Sequence–Specific DNA–Binding Protein, Cell 65:1073–1082, 1991.
Christy and Nathans, Functional Serum Response Elements Upstream of the Growth Factor–Inducible Gene zif268, Mol. Cell. Biol. 9:4889–4895, 1989.
Clarke et al., Requirement for a Functional Rb–1 Gene in Murine Development, Nature 359:328–333, 1992.
DeCaprio et al. SV40 Large Tumor Antigen Forms a Specific Complex with the Product of the Retinoblastoma Susceptibility Gene, Cell 54:275–283, 1988.
Devoto et al., A Cyclin A–Protein Kinase Complex Possesses Sequence–Specific DNA Binding Activity: $p33^{cdk2}$ is a Component of the E2F–Cyclin A Complex, Cell 68:167–176, 1992.
Dowdy et al., Physical Interaction of the Retinoblastoma Protein with Human D Cyclins, Cell 73:499–511, 1993.
Ewen et al., An N–Terminal Transformation–Governing Sequence of SV40 Large T Antigen Contributes to the Binding of Both $p110^{Rb}$ and a Second Cellular Protein, p120, Cell 58:257–267, 1989.
Ewen et al., Functional Interactions of the Retinoblastoma Protein with Mammalian D–type Cyclins, Cell 73:487–497, 1993.
Fingar et al., Dissociation of pp70 Ribosomal Protein S6 Kinase from Insulin–stimulated Glucose Transport in 3T3–L1 Adipocytes, J. Biol. Chem. 268:3005–3008, 1993.
Flemington et al., E2F–1–mediated Transactivation is Inhibited by Complex Formation with the Retinoblastoma Susceptibility Gene Product, Proc. Natl. Acad. Sci. USA 90:6914–6918, 1993.
Garvey et al., Pretranslational Suppression of an Insulin–Responsive Glucose Transporter in Rats with Diabetes Mellitus, Science 245:60–63, 1989.

(List continued on next page.)

Primary Examiner—Paul J. Killos
Attorney, Agent, or Firm—Fish & Richardson

[57] ABSTRACT

The invention features methods of treating insulin–induced obesity, weight gain, and other conditions associated with hyperinsulinemia.

18 Claims, 7 Drawing Sheets

OTHER PUBLICATIONS

Gerrits et al., Regulation of the GLUT4/Muscle–fat Glucose Transporter mRNA in Adipose Tissue of Insulin–deficient Diabetic Rats, J. Biol. Chem. 268:640–644, 1993.

Gilman et al., Multiple Protein–Binding Sites in the 5'–Flanking Region Regulate c–fos Expression, Mol. Cell. Biol. 6:4305–4316, 1986.

Girling et al., A New Component of the Transcription Factor DRTF1/E2F, Nature 362:83–87, 1993.

Gorski et al., Tissue–Specific In Vitro Transcription from the Mouse Albumin Promoter, Cell 47:767–776, 1986.

Greenberg et al., Effect of Protein Synthesis Inhibitors on Growth Factor Activation of c–fos, c–myc, and Actin Gene Transcription, Mol. Cell. Biol. 6:1050–1057, 1986.

Helin et al., A cDNA Encoding a pRB–Binding Protein with Properties of the Transcription Factor E2F, Cell 70:337–350, 1992.

Hiebert, Regions of the Retinoblastoma Gene Product Required for Its Interaction with the E2F Transcription Factor are Necessary for E2 . . . pRb–Mediated Growth Suppression, Mol. Cell. Biol. 13:3384–3391, 1993.

Hill et al., Functional Analysis of a Growth Factor–Responsive Transcription Factor Complex, Cell 73:395–406, 1993.

Hinds et al., Regulation of Retinoblastoma Protein Functions by Ectopic Expression of Human Cyclins, Cell 70:993–1006, 1992.

Huang et al., Two Distinct and Frequently Mutated Regions of Retinoblastoma Protein are Required for Binding to SV40 T Antigen, EMBO J. 9:1815–1822, 1990.

Huber et al., Transcription Factor E2F Binds DNA as a Heterodimer, Proc. Natl. Acad. Sci. USA 90:3525–3529, 1993.

Jacks et al., Effects of an Rb Mutation in the Mouse, Nature 359:295–302, 1992.

Kaelin et al., Definition of the Minimal Simian Virus 40 Large T Antigen– and Adenovirus E1A–Binding Domain in the Retinoblastoma Gene Product, Mol. Cell. Biol. 10:3761–3769, 1990.

Kahn, Facilitative Glucose Transporters: Regulatory Mechanisms and Dysregulation in Diabetes, J. Clin. Invest. 89:1367–1374, 1992.

Kahn et al., Differential Regulation of Two Glucose Transporters in Adipose Cells from Diabetic and Insulin–treated Diabetic Rats, J. Clin. Invest. 84:404–411, 1989.

Kato et al., Direct Binding of Cyclin D to the Retinoblastoma Gene Product (pRb) and pRb Phosphorylation by the Cyclin D–dependent Kinase CDK4, Genes & Development 7:331–342, 1993.

Krek et al., Binding to DNA and the Retinoblastoma Gene Product Promoted by Complex Formation of Different E2F Family Members, Science 262:1557–1560, 1993.

Lee et al., Mice Deficient for Rb are Nonviable and Show Defects in Neurogenesis and Haematopoiesis, Nature 359:288–294, 1992.

Lees et al., The Retinoblastoma Protein Binds to a Family of E2F Transcription Factors, Mol. Cell. Biol. 13:7813–7825, 1993.

Liu et al., Expression and Regulation of the Human GLUT4/Muscle–Fat Facilitative Glucose Transporter Gene in Transgenic Mice, J. Biol. Chem. 267:11673–11676, 1992.

Marais, et al., The SRF Accessory Protein Elk–1 Contains a Growth Factor–Regulated Transcriptional Activation Domain, Cell 73:381–393, 1993.

McClain et al., Dissection of the Growth versus Metabolic Effects of Insulin and Insulin–like Growth Factor–I in Transfected Cells Expressing Kinase–defective Human Insulin Receptors, J. Biol. Chem. 265:1678–82, 1990.

Morice et al., Rapamycin Inhibition of Interleukin–2–dependent $p33^{cdk2}$ and $p34^{cdc2}$ Kinase Activation in T Lymphocytes, J. Biol. Chem. 268:22737–22745, 1993.

Mudryj et al., Cell Cycle Regulation of the E2F Transcription Factor Involves an Interaction with Cyclin A, Cell 65:1243–1253, 1991.

Mudryj et al., A Role for the Adenovirus Inducible E2F Transcription Factor in a Proliferation Dependent Signal Transduction Pathway, EMBO J. 9:2179–2184, 1990.

Nasrin et al., An Insulin Response Element in the Glyceraldehyde–3–phosphate Dehydrogenase Gene Binds a Nuclear Protein Induced . . . Nutritional Manipulations in vivo, Proc. Natl. Acad. Sci. USA 87:5273–77, 1990.

Nasrin et al., DNA–binding Properties of the Product of the Testis–determining Gene and a Related Protein, Nature 354, 317–320, 1991.

Olson et al., Hormonal/Metabolic Regulation of the Human GLUT4/Muscle–fat Facilitative Glucose Transporter Gene in Transgenic Mice, J. Biol. Chem. 268:9839–9846, 1993.

Price et al., Rapamycin–Induced Inhibition of the 70–Kilodalton S6 Protein Kinase, Science 257:973, 1992.

Qian et al., Biological Function of the Retinoblastoma Protein Requires Distinct Domains for Hyperphosphorylation and Transcription Factor Binding, Mol. Cell. Biol. 12:5363–5372, 1992.

Sadowski et al., A Common Nuclear Signal Transduction Pathway Activated by Growth Factor and Cytokine Receptors, Science 261:1739–1744, 1993.

Shirodkar et al., The Transcription Factor E2F Interacts with the Retinoblastoma Product and a p107–Cyclin A Complex in a Cell Cycle–Regulated Manner, Cell 68:157–166, 1992.

Sivitz et al., Regulation of Glucose Transporter Messenger RNA in Insulin–deficient States, Nature 340:72–74, 1989.

Taub et al., Insulin as a Growth Factor in Rat Hepatoma Cells, J. Biol. Chem. 262:10893–10897, 1987.

Tsai–Morris et al., 5' Flanking Sequence and Genomic Structure of Egr–1, a Murine Mitogen Inducible Zinc Finger Encoding Gene, Nucleic Acids Research, 16:8835–8846, 1988.

Weintraub et al., Retinoblastoma Protein Switches the E2F Site from Positive to Negative Element, Nature 358:259–261, 1992.

Whyte et al., Association Between an Oncogene and an Anti–Oncogene: the Adenovirus E1A Proteins Bind to the Retinoblastoma Gene Product, Nature 334:124–129, 1988.

Wyhte et al., Cellular Targets for Transformation by the Adenovirus E1A Proteins, Cell 56:67–75, 1989.

Wilden et al., The Insulin Receptor with Phenylalanine Replacing Tyrosine–1146 Provides Evidence for Separate Signals Regulating Cellular Metabolism and Growth, Proc. Natl. Acad. Sci. USA 87:3358–3362, 1990.

Zamanian and La Thangue, Adenovirus E1a Prevents the Retinoblastoma Gene Product from Repressing the Activity of a Cellular Transcription Factor, EMBO J. 11:2603–2610, 1992.

Zhang et al., Normal and Oncogenic $p21^{ras}$ Proteins Bind to the Amino–terminal Regulatory Domain of c–Raf–1 Nature 364:308–313, 1993.

Zhu et al., Inhibition of Cell Proliferation by p107, a Relative of the Retinoblastoma Protein, Genes & Development 7:1111–1125, 1993.

INHIBITION OF INSULIN-INDUCED ADIPOSIS

BACKGROUND OF THE INVENTION

This invention relates to the treatment of insulin-induced obesity, weight gain, and other conditions associated with hyperinsulinemia.

Lipogenesis is the cardinal adaptive response to excess carbohydrate. Faced with a carbohydrate load, an animal mounts a response in liver and adipose tissue that re-orients cellular metabolism to facilitate the uptake of glucose and other nutrients from the circulation, and their conversion into energy storage molecules such as glycogen and fat. Insulin is the major hormone charged with coordinating these responses.

Current methods for treating obesity include behavior modification programs, very low calorie diets, surgery (gastroplasty), and administration of appetite suppressants.

SUMMARY OF THE INVENTION

The invention features a method of treating insulin-stimulated obesity. In this method, an adult (i.e., a person 18 years of age or older) identified as being in need of such treatment is administered an amount of rapamycin (or an analog thereof) effective to inhibit insulin-induction of glyceraldehyde-3-phosphate dehydrogenase (GAPDH), acetyl CoA carboxylase, or the major insulin-sensitive glucose transporter (GLUT4) gene expression in his or her cells (e.g., in his or her adipocytes and/or hepatocytes). An animal, e.g., a human adult, is described herein as being "obese" if he or she has a body weight 20% or more over that which is considered to be a normal body weight for the animal, as determined by one skilled in the art. An amount of rapamycin is said to be effective at inhibiting insulin-induced expression of GAPDH, acetyl CoA carboxylase, or GLUT4 in a given cell or tissue if it effects a decrease to 50% or less of the level of insulin-induced gene expression that occurs in that cell or tissue in the absence of rapamycin treatment. Preferably, the treatment with rapamycin reduces the expression to 25%; more preferably the treatment reduces the expression to 10%; and most preferably the treatment reduces the expression to less than 1% of that observed in the absence of rapamycin. In one embodiment of this aspect of the invention, the adult has, or is at risk of developing, type II diabetes. In another embodiment, the adult has, or is at risk of developing, hyperinsulinemia.

In another aspect, the invention features a method of inhibiting weight gain in a patient. In this method, a patient identified as being need of prevention of weight gain resulting from hyperinsulinemia is administered an amount of rapamycin effective to reduce this weight gain. An amount of rapamycin is described as being effective at reducing the weight gain in such a patient, if administration of this amount results in a weight gain that is less than about 50% of that which would have been expected to occur in the patient in the absence of rapamycin treatment. Preferably, the amount of weight gain is reduced by about 75%; and most preferably, it is reduced to approximately zero. In one embodiment of this aspect of the invention, the hyperinsulinemia is attributable to exogenous insulin administered to the patient, as in the management of a diabetic condition. In another embodiment, the hyperinsulinemia is attributable to abnormally high levels of endogenous insulin in the patient, as determined by one skilled in the art.

In another aspect, the invention features a method of treating complications of hyperinsulinemia attributable to the chronically high levels of insulin in the blood of the patient. In this method, a patient identified as needing such treatment is administered an amount of rapamycin effective to inhibit insulin-induction of GAPDH, acetyl CoA carboxylase, or GLUT4 gene expression in the patient.

The modes of administration used in the methods of the invention include, but are not limited to, enteral, parenteral, and transmucosal administration, and that accomplished by inhalation (e.g., of aerosol mist or powder) or implant. The term parenteral as used herein includes, but is not limited to, subcutaneous, intravenous, intramuscular, intraperitoneal, and intrasternal injection and infusion techniques, which are well known in the art. The preferred method of administration is oral.

In another aspect, the invention features a method of inhibiting an insulin-stimulated increase in fat content in a cell, e.g., an adipocyte or an hepatocyte, by contacting the cell with an amount of rapamycin effective to inhibit induction of GAPDH, acetyl CoA carboxylase, or GLUT4 gene expression in the cell. The cell may be in an animal e.g., a mammal, such as a human, cow, horse, pig, dog, cat, sheep, goat, rabbit, rat, guinea pig, hamster, or mouse. In one embodiment, the animal has, or is at risk of developing, hyperinsulinemia. In another embodiment, the animal has, or is at risk of developing, type II diabetes. In yet another embodiment, the animal has, or is at risk of developing, obesity.

In a final aspect, the invention features a therapeutic composition containing insulin and rapamycin, present in amounts determined by one skilled in the art. The therapeutic composition may further contain a pharmaceutically acceptable carrier or diluent. Such a composition may be administered by any medically acceptable route, e.g., by subcutaneous injection, and is useful for management of a diabetic condition.

Other features and advantages of the invention will be apparent from the following detailed description, the drawings, and the claims.

BRIEF DESCRIPTION OF THE DRAWINGS

FIG. 1A is a Northern blot of RNA isolated from 3T3-F 442A preadipocytes and adipocytes. 3T3-F442A preadipocytes were grown to 50% confluence and exposed to 1 mU/ml insulin or no agonist. 3T3-F442A cells were grown to confluence, differentiated, and then were exposed to 1 mU/ml insulin or no agonist. Total RNA (20 µg) was isolated from the cells and subjected to Northern analysis. Total RNA was transferred to Genescreen and hybridized with random primed cDNAs encoding Egr-1 or GAPDH.

FIG. 1B is a Northern blot of RNA isolated from epididymal adipose and heart tissue. Epididymal fat cells or whole heart muscle was isolated from control rats (C), rats treated with streptozotocin (D) for 7 days, or rats treated with streptozotocin for 7 days followed by insulin for 7 days (D/I) (Kahn, et al., J. Clin. Invest., 84:401–411, 1989; Charron and Kahn, J. Biol. Chem., 265:7994–8000, 1990). Nucleic acids were extracted with guanidinium isothiocyanate, and the RNA was purified by centrifugation through a cesium chloride cushion. Total RNA (20 µg) was subjected to formaldehyde agarose gel electrophoresis. RNA was transferred to Genescreen and hybridized with random primed cDNAs encoding Egr-1 (Sukhatme, et al., Oncogene Res., 1:343–355, 1988), c-fos, GAPDH, or GLUT4. The blots are representative of four experiments. Lanes 1–3, adipose RNA isolated from control, diabetic, or insulin-treated diabetic animals, respectively. Lanes 4–6, muscle mRNA isolated from the same control, diabetic, or insulin-treated diabetic animals is shown.

FIG. 3 is a CAT assay of stably transfected H35 hepatoma cells. Two stable H35 hepatoma cell lines, one transfected with the HGAPDH (−487 to +20) -CAT gene, and the other transfected with Egr-1 (−935 to +248) -CAT, were plated and grown to confluence. Cells were starved in the presence of 0.1% crystalline BSA and DMEM. During the last 16 hours of the incubation, insulin was added at a final concentration of 1 mU/ml in the presence and absence of rapamycin, as indicated. CAT activity is shown corrected for protein concentration.

FIG. 4B is an electrophoretic mobility shift assay (EMSA) showing competition of the liver IRP-A complex with the cognate E2 DNA binding motif. Nuclear extracts isolated from fasted (3 μg) or fasted-refed (3 μg) liver were incubated with $^{32}$P-labelled IRE-A, or $^{32}$P-labelled DNA and a 200-fold excess of competitor DNA, as described for EMSA gel assays in Methods. Lanes 1–7: 32P-labelled IRE-A DNA; lane 1, fasted nuclear extract; lanes 2–7, fasted-refed nuclear extract; lanes 1 and 2, nonspecific oligonucleotides; lane 3, wild-type IRE-A DNA; lane 4, mutant IRE-A (GC→TA) DNA; lane 5, wild-type E2 DNA; lane 6, mutant E2 (GC→TA) DNA; lane 7, DRTF DNA. Lanes 8–14: 32P-labelled E2 DNA; lane 8, fasted nuclear extract; lanes 9–14, refed nuclear extract; lanes 8 and 9, nonspecific oligonucleotides; lane 10, wild-type IRE-A DNA; lane 11, mutant IRE-A (GC→TA) DNA; lane 12, wild-type E2 DNA; lane 13, mutant E2 (GC→TA) DNA; lane 14, DRTF DNA.

FIG. 4C is an electrophoretic mobility shift assay showing IRP-A and GST-RBAP-1 complexes with IRE-A DNA. GST-RBAP-1 (lanes 1–3) or nuclear proteins isolated from fasted-refed liver nuclear extract (lanes 4–6) were incubated with $^{32}$P-labelled IRE-A DNA in the presence of: lanes 1 and 4, mutant IRE-A DNA (GC→TA); lanes 2 and 5, wild-type E2 DNA; and, lanes 3 and 6, mutant E2 DNA (GC→TA) as described above.

FIG. 4D is a methylation interference assay of the IRP-A and GST-RBAP-1 complexes with IRE-A DNA. The IRP-A complex (lane 2) was formed with fasted-refed liver nuclear extract and premethylated $^{32}$P-labelled IRE-A DNA. The RBAP 1 complex was formed with GST-RBAP-1 and premethylated 32p_ labelled IRE-A DNA (lane 3). Lanes 1 and 4: a completed G reaction on the IRE-A DNA probe (−487 to −408 from the HGAPDH gene). The contact points (gag-gcgggaaag; SEQ ID NO: 1) are indicated with an asterisk.

FIG. 5A is a graph showing the effect of E2F-1 on IRE-A-CAT transcription in L6 cells. A tetramer of the minimal IRE-A binding site was fused to the GAPDH promoter (−40 to +20), which contains one E2F site at the TATAA box. The HGAPDH-CAT (8 μg/ml) and RSV-GH (8 μg/ml) plasmids were cotransfected with CMV (2μg/ml) or CMV-E2F (2μg/ml) into L6 cells using the calcium phosphate transfection protocol as described in Methods. From left to right, the constructs shown are: −40 to +20 alone, wild-type IRE-Ax4, and the Δ5'IRE-Ax4 mutation, fused to nucleotides −40 to +20 of the GAPDH promoter.

CAT activity, GH activity, and protein concentrations were measured.

FIG. 6C is a graph showing that T antigen inhibits the effect of insulin on the expression of HGAPDH-CAT. Human GAPDH-CAT (−487 to +21) (8 μg/ml) and RSV-GH (6 μg/ml) were cotransfected into H35 hepatoma cells with (2 μg/ml) wild-type $T_{Ag}$ or a mutant $T_{Ag}$ referred to as $K_1$. The cells were grown to confluence, serum-starved overnight in the presence and absence of insulin (1 mU/ml), harvested, and CAT activity analyzed as described in Methods.

FIG. 7 is a Western blot showing that Rb (retinoblastoma) is hyperphosphorylated in insulin-treated H35 hepatoma whole cell lysates. H35 hepatoma cells were grown to confluence and deprived of serum for 24 hours before stimulation with no agonist, insulin (10 nM), TPA (300 nM), or serum (10%). Thirty minutes before the addition of agonists, either ethanol (lanes 1–4) or rapamycin (1 nM) (lanes 5–8) was added to the cells. Cells were lysed in boiling SDS/urea lysis buffer and the lysates (100 mg protein) resolved by SDS-PAGE in 7.5% gels, followed by transfer to nitrocellulose. The membranes were incubated with an antibody raised against human Rb (PMG3–245). Lanes 1 and 5 contain lysates from control cells; lanes 2 and 6 contain lysates from cells stimulated with insulin for 16 hours; lanes 3 and 7, lysates from cells stimulated with TPA for 16 hours; and lanes 4 and 8, lysates from cells stimulated with serum for 16 hours. The position of migration of hypophosphorylated (light arrow) and hyperphosphorylated (bold arrow) Rb are indicated. Similar results were obtained in three other experiments.

DETAILED DESCRIPTION

The invention provides methods for treating patients identified as having hyperinsulinemia (or a condition associated with hyperinsulinemia, to the extent that inhibiting the rapamycin-sensitive pathway of insulin-induced gene expression results in an improvement in the condition). These methods involve administration of rapamycin, or an analog of rapamycin which acts on the same pathway of insulin-induced gene expression (as determined, for example, by the assays described below), to a patient in need of treatment for one of the above-described conditions. The methods of the invention can also be used to prevent the onset of these conditions in patients identified as being at risk for developing them.

Rapamycin inhibits insulin-induced expression of genes involved in uptake of carbohydrate and biosynthesis of triglycerides, including GAPDH, GLUT4, and acetyl CoA carboxylase. In a patient subject to hyperinsulinemia, detection of a decrease in weight gain or obesity following treatment in accordance with the invention indicates an underlying decrease in expression of one or more of these genes. Decreases in weight gain or obesity can be detected using any appropriate method known to those skilled in the art. For example, obesity can be measured by determining the body mass index (BMI; Agras, Chapter III, Scientific American, Rubenstein et al., (eds.) (New York 1978) pp. 1–14), which is the ratio of the weight (in kilograms) to the square of the height (in meters) of the subject. Treatment to decrease body fat is generally recommended for women with a BMI of above 27, and men with a BMI above 28. Determining the waist-to-hip ratio is another method for diagnosing obesity. A waist-to-hip ratio of greater than 1.0 in women, and 0.8 in men, is associated with an increased risk for cardiovascular disease, and is an indication for treatment of obesity.

Examples of the hyperinsulinemia-associated conditions that can be treated or prevented using the methods of the invention include, but are not limited to, obesity, type II diabetes mellitus and complications thereof, ovarian syndromes that lead to excessive androgen secretion (e.g., polycystic ovary syndrome which is characterized by infertility, hirsutism, insulin resistance, amenorrhea, abnormal bleeding, obesity, and, occasionally, virilism), and any insulin-dependent tumors (e.g., lipomas). In addition, any diseases and conditions associated with increased levels of insulin-like growth factor (IGF), e.g., breast cancer, can be treated using the methods of the invention, to the extent that the IGF receptor implicated in the condition acts via the same pathway of signal transduction shown herein to be rapamycin-sensitive.

Obesity is frequently associated with a number of diseases and conditions, including, but not limited to Cushing's syndrome, hypothalamic injury or tumor, hypothyroidism, type II diabetes mellitus or impaired glucose tolerance, congestive heart failure, elevated cholesterol and triglyceride levels, coronary artery disease, gallbladder disease, pulmonary dysfunction (including sleep apnea), osteoarthritis, hypertension, and polycystic ovary syndrome. To the extent that the weight gain or obesity associated with these conditions is attributable to an insulin-sensitive mechanism, the methods of the invention may be used, either alone or in combination with the conventional treatments for these diseases and conditions, to ameliorate the weight gain or obesity. Methods well known in the art can be used to determine whether a patient has, or is at risk of developing, any of the above-described conditions.

A number of medications are known to cause or contribute to weight gain or obesity. For example, patients being treated with tricyclic antidepressants (e.g., imipramine, desipramine, and trazodone), phenothiazines (e.g., chlorpromazine, thioridazine, and haloperidol), steroids, and antiepileptic agents (e.g., valproic acid and carbamazepine) (Agras, Chapter III, Scientific American, Rubenstein et al., (eds.) (New York 1978) pp. 1–14), frequently experience weight gain as a side effect of the treatment. To the extent that the weight gain or obesity associated with these medications is mediated by insulin, the methods of the invention may be used to ameliorate these side effects.

Analogs and derivatives of rapamycin, including, but not limited to, 0-Aryl, 0-Alkyl, 0-Alkenyl, and 0-Alkynyl rapamycins (U.S. Pat. No. 5,258,389; which is herein incorporated by reference), and other related macrocyclic compounds (see, e.g., the compounds described in PCT Patent WO 93/16083; PCT Patent WO 92/00313; U.S. Pat. No. 5,252,732; and U.S. Pat. No. 5,247,076; each of which is herein incorporated by reference) may also be used in the methods of the invention. Any rapamycin analog can be tested for effectiveness either in vitro (as described herein for rapamycin), or in vivo in an animal model, using standard methods.

The therapeutic compositions used in the methods of the invention may be used alone, or in admixture or chemical combination with one or more materials. The therapeutic compositions may be administered in a pharmaceutically acceptable carrier (e.g., physiological saline), which is selected on the basis of the mode and route of administration, and standard pharmaceutical practice. Suitable pharmaceutical carriers, as well as pharmaceutical necessities for use in pharmaceutical formulations, are described in Remington's Pharmaceutical Sciences, a standard reference text in this field, and in the USP/NF. The therapeutic compositions may be administered to a patient by any appropriate mode, e.g., orally, parenterally, or transmucosally, or by inhalation, as determined by one skilled in the art. Alternatively, it may be desirable to administer the treatment surgically to the target tissue, in, e.g., the form of an implant.

The therapeutic compositions used in the methods of the invention can be administered in dosages determined to be appropriate by one skilled in the art. An appropriate dosage is one which effects a reduction in obesity or weight gain, or in the target condition or disease associated with hyperinsulinemia and/or obesity. It is expected that the dosages will vary, depending upon the activity of the specific rapamycin-like compound employed, the mode and route of administration, as well as the age, weight, sex, diet, and health of the recipient; the nature and extent of the disease; the frequency and duration of the treatment; the time of administration; the rate of excretion; the type of, if any, concurrent therapy; and the desired effect. Dosage levels of the compounds used in the therapeutic methods of the present invention are of the order from about 0.005 mg to about 50 mg per kilogram of body weight per day, preferably from about 0.1 mg to about 20 mg per kilogram of body weight per day, and most preferably 6 mg to about 12 mg per kilogram of body weight per day. In addition, the compounds of the present invention may be administered on an intermittent basis: i.e., at daily, semi-weekly, weekly, semi-monthly, or monthly intervals. It may be desirable to administer the compounds at or immediately after each meal, when the endogenous insulin level in the blood naturally increases dramatically.

EXPERIMENTAL DATA

MATERIALS AND METHODS
Construction of Plasmids

Construction of HGAPDH-CAT has been previously described (Alexander, et al., Proc. Natl. Acad. Sci. USA, 85:5092–5096, 1988). Briefly, HGAPDH-CAT contains a TAQ-TAQ fragment which includes nucleotides −487 to +21 of the HGAPDH promoter cloned into the ACCI site of PUC-CAT. A truncated GAPDH-CAT construct containing nucleotides −116 to +21 of the GAPDH promoter was prepared by digesting PUC-CAT with SALI, forming blunt ends, and then digesting with XBAI. A STUI-XBA fragment that contained nucleotides −116 to +21 of the GAPDH promoter was isolated from HGAPDH-CAT and ligated to PUC-CAT as described above. A truncated human GAPDH-CAT construct was made by subcloning a fragment containing −55 to +21 of the HGAPDH promoter into the SALI and XBAI sites of a PUCCAT vector. A tetramer of the minimal sequence within the IRE-A element that supports binding of the IRP-A complex (−480 to −435) was subcloned into the Hind III site of both truncated HGAPDH promoter constructs. The E2F site within IRE-A, TTTCCCGCCTC (SEQ ID NO: 2), is located on the 5' end of the IRE-A motif. The 5' mutation that destroys E2F binding CCCTACTC (SEQ ID NO: 3) is indicated as a GC→TA mutation.

There is at least one E2F binding site within the minimal promoter (−55 to +21) and additional sites between −55 to −116. The sites between −54 to −116 obscure the effect of exogenous E2F in L6 cells. Thus, constructs with IRE-A fused to the minimal promoter fragment (−55 to +21) were used to demonstrate the effect of E2F-1 in L6 muscle cells. It is preferable to use constructs that contain the minimal promoter −54 to +20 for studies of insulin action as well, since there is no insulin effect on this fragment in the absence of IRE-A sites. Nevertheless, because it was difficult to detect expression of plasmids containing −55 to +20 of the HGAPDH promoter in H35 hepatoma cells, plasmids containing −116 to +20 of the HGAPDH promoter were used for these experiments.

CMV-RBAP-1, GST-RBAP-1, GAL4-E2F-1, and GAL4-E2F-2 (Kaelin, et al., Cell, 70:351–364, 1992; Flemington, et al., Proc. Natl. Acad. Sci. USA, 90:6914–6918, 1993), wild-type simian virus 40 large T antigen, the K1 mutant of T antigen that does not bind p107/Rb (Ewen, et al., Cell, 58:257–267, 1989), PG5EC-CAT, and GAL4-VP-16 (Sadowski et al., Nucleic Acid Res., 17:7539, 1989) are as described elsewhere.

RNA Isolation and Northern Blot Analysis

RNA was isolated as previously described (Alexander, et al., J. Biol. Chem., 260:11978–11985, 1985). Briefly, 3T3-F442 cells were grown to confluence and differentiated (Alexander, et al., J. Biol. Chem., 260:11978–11985, 1985). Growing 3T3-F442A cells and differentiated 3T3-F442A cells were serum starved in 1% fetal bovine serum (FBS) overnight in the presence or absence of insulin for the times indicated. To isolate RNA, the cells were lysed in buffer containing 10 mM Tris·HCL (pH 7.4), 0.15 M NaCl, 3 mM $MgCl_2$, 0.5% Triton X-100, 1 mM DTT, and 10 mM Vanadyl ribonucleotide complex. After centrifugation at 3000 rpm for 5 minutes, protein was removed from the supernatant by extraction with phenol and chloroform, and the RNA was precipitated with ethanol. Twenty micrograms of total RNA was denatured in 50% formamide and 2.2 M formaldehyde, then separated on 1.4% formaldehyde gels. RNA was transferred to nitrocellulose. The blots were hybridized with GAPDH, GLUT4, Egr-1 and c-fos cDNA probes.

RNA was isolated from control, streptozotocin-treated diabetic, and insulin-treated diabetic animals using the guanidinium isothiocyanate method previously described (Kahn, et al., J. Clin. Invest., 89:1367–1374, 1989; Maniatis, et al., 1982). Formaldehyde gel electrophoresis was performed as previously described (Kahn, et al., J. Clin. Invest., 89:1367–1374, 1989). Several Northern blots previously used to examine the pattern of GLUT4 gene regulation in fat and muscle of diabetic and insulin-treated animals were hybridized with GAPDH (Alexander et al., J. Biol. Chem., 260:11978–11985, 1985), c-fos, and Egr-1 (Sukhatme et al., Oncogene Res., 1:343–355, 1988) cDNA probes for comparative purposes. A representative sample is shown in which RNA is matched for cell number in the case of fat and for DNA in muscle.

H35 hepatoma cells were grown to confluence in Dulbecco's modified Eagle's medium (DMEM) supplemented with 10% FBS and 2 mM glutamine. The cells were serum starved in DMEM containing 0.1% bovine serum albumin (BSA) and 10 mm HEPES (pH 7.4) for 24 to 48 hours, and then exposed to agonists for the times indicated in the figures. Anisomycin was added for 30 minutes prior to the addition of insulin. RNA was isolated described above (Alexander et al., J. Biol. Chem., 260:11978–11985, 1985).

Cell Culture and Transfection Assays

Stable lines: Pooled stable H35 hepatoma cell lines expressing a human GAPDH-CAT fusion gene containing nucleotides −487 to +20, an Egr-1-CAT fusion gene containing nucleotides −935 to +360, or an RSV-CAT reporter gene and the neomycin-resistance gene, were selected with G418 (Alexander et al., Proc. Natl. Acad. Sci. USA, 85:5092–5096, 1988). Each line was grown to confluence in DMEM medium with 10% fetal bovine serum and 2 mM glutamine. Prior to the addition of hormones, the medium was changed to DMEM containing 0.1% BSA and 10 mM HEPES (pH 7.4). After 10–16 hours, the cells were stimulated with or without 1 milliunit/ml insulin for 16 hours. When rapamycin was used, ethanol or rapamycin (Drug Synthesis & Chemistry Branch, Developmental Therapeutics Program, Division of Cancer Treatment, National Cancer Institute) was added 30 minutes prior to the addition of insulin, as indicated in the figures.

Transient transfection: H35 hepatoma cells were grown in 35 mm dishes to 70% confluence in Dulbecco's modified Eagle's medium (DMEM) supplemented with 10% fetal bovine serum and 2 mM glutamine. Reporter plasmid (2.6 μg) and factor DNA (500 ng) were co-transfected with 1.3 μg of a human growth hormone construct (RSV-GH) per 35 mm dish using the calcium phosphate mediated DNA transfer procedure (Nasrin, et al., Proc. Natl. Acad. Sci. USA, 87:5273–5277, 1990). The next day, the cells were washed twice with phosphate-buffered saline, and changed to DMEM supplemented with 0.1% bovine serum albumin, 2 mM glutamine, and 10 mM Hepes. After 10 hours, the cells were stimulated with or without insulin (final concentration of 1 milliunit/ml) and incubated for 16 hours. Growth hormones in the gene mechanism was measured using a Nichols RIA kit. The cells were harvested, and CAT activity was detected as previously described (Alexander et al., Proc. Natl. Acad. Sci. USA, 85:5092–5096, 1988).

L6 muscle cells were grown in 35 mm dishes to 70% confluence in a-Minimum Essential Medium (a-MEM) supplemented with 2% FBS. The reporter plasmid (2.5–5 μg) was co-transfected with 2 μg RSV-GH and 500 ng factor DNA per 35 mm dish using the calcium phosphate mediated DNA transfer procedure (Nasrin, et al., Proc. Natl. Acad. Sci. USA, 87:5273–5277, 1990). After 14 hours of incubation, the cells were shocked for 1 minutes by 10% DMSO in 1X PBS. The cells were fed in the above culture medium. The next day, cells were harvested, and CAT activity measured as described above.

CHO-HIR cells (stably transfected with the human insulin receptor) were grown in 35 mm dishes to 60% confluence in F-12 Hams medium supplemented with 10% FBS and 2 mM glutamine. Reporter plasmid (3.75 μg), 1.75 μg of β-galactosidase (RSV-β-Gal), and factor DNA (12.5 ng) per 35 mM dish were cotransfected using the calcium phosphate-mediated DNA transfer procedure described above. After 4 hours, the cells were shocked with 20% glycerol for 3 minutes, washed twice with PBS, and maintained in medium for a total of 48 hours, at which point they were harvested. Cell lysates were used to estimate CAT activity as described below. Cell lysates were used to measure β-galactosidase levels (Sambrook, et al., Cold Spring Harbor Laboratory, Cold Spring Harbor, pp. 16.66–16.67, 1989). A standard curve was generated using β-galactosidase obtained from Boehringer Mannheim.

CAT Activity Assay

The acetylated form of chloramphenicol was separated by thin-layer chromatography using 95% chloroform, 5% methanol as the solvent. The percent of total [14-C]-chloramphenicol acetylated (per 100 μg of extract protein) was calculated and normalized for expression of growth hormone in the medium.

Preparation of nuclear extracts

Nuclear extracts were isolated from the nuclei of epididymal fat cells using a modification of the Dignam procedure previously described for 3T3-F442A adipocytes (Dignam, et al., Nucleic Acid Res., 2:1475–1489, 1983; Nasrin, et al., Proc. Natl. Acad. Sci. USA, 87:5273–5277, 1990). The cells were lysed in buffer A containing 10 mM HEPES (pH 7.9), 1.5 mM MgCl$_2$, 100 mM KCL, and 0.5 mM dithiothreitol. Proteinase and endogenous phosphatase inhibitors (0.5 mM PMSF, 25 mM NaF, 20 μM leupeptin, 20 μM pepstatin, 100 kallikrein units of Trasylol/ml, and 2 mM sodium vanadate) were added, then the cells were homogenized using a Dounce homogenizer. The cells were centrifuged for 10 minutes at 10,000 rpm. The pellets were stirred for 30 minutes in an extraction buffer containing 20 mM HEPES, 20% glycerol, 0.42 M NaCl, 1.5 mM MgCl$_2$, 0.2 mM EDTA, 1 mM PMSF, 50 mM NaF, 1 mM NaV04, and 1 mM DTT. The extracts were centrifuged for 60 minutes at 18,000 rpm. The supernatant was removed and dialyzed in butter D containing 20 mM HEPES, 20% glycerol, 0.1 M KCL, 0.2 mM EDTA, 0.5 mM PMSF, and 0.5 mM DTT.

The rats were fasted for 48 hours, or fasted and then refed with a high-carbohydrate, low-fat diet. The nuclear protein was extracted described by Gorski, et al. (Gorski, et al., Cell, 47:767–776, 1986). Two rat livers were homogenized in a total volume of 90 mls of homogenization buffer (10 mM HEPES (pH 7.6), 25 mM KCl, 1 mM EDTA, 10% glycerol, 1 mM DTT, 1 mM PMSF, and 2 M sucrose) and layered in three 27 ml aliquots over three 10 ml cushions of the same buffer. The samples were centrifuged at 24,000 rpm for 30 minutes at 4° C. in an SW-27 rotor. Each pellet containing the nuclei was resuspended in 10 mls of lysis buffer (10 mM HEPES (pH 7.6), 10 mM KCl, 3 mM MgCl2, 0.1 mM EDTA, 5 mM DTT, 0.1 mM PMSF, and 10% glycerol) using a Dounce homogenizer. 1/10th volume of 4M (NH4)2SO4 pH 7.9 saturated with NaOH was added dropwise with gentle stirring for 30 minutes. The lysate was then centrifuged at 20,000 rpm for 60 minutes at 0° C. Solid (NH4)2SO4 at a concentration of 0.3 g/ml was slowly added to the supernatant with gentle stirring for slow dissolution. The precipitated protein was centrifuged at 35,000 rpm, then resuspended in dialysis buffer (20 mM HEPES (pH 7.9), 100 mM KCl, 0.2 mM EDTA, 1 mM DTT, 20% glycerol, 1 mM PMSF, 20 μM leupeptin, 2 μM pepstatin, 10 KU Trasylol/ml). The protein extract was dialyzed for 2 hours at 4° C. in the same buffer. Extracts were stored at −80° C. or in liquid nitrogen.

Preparation of GST-Fusion Proteins

Overnight cultures of bacteria transformed with a glutathione expression vector, PGEX-GT, or glutathione fusion genes encoding GST-RBAP-1 derivatives were diluted 1:10 in L broth supplemented with 50 μg/ml ampicillin and grown for 1 hour at 37° C. After induction with 1 mM isopropyl-b-D-thiogalactoside (IPTG) for 3 hours, cells were pelleted by centrifugation at 5,000 g, and extracted with guanidine-HCl as previously described (Nasrin, et al., Nature, 354:317–320, 1991) with the following modifications. Pelleted cells were lysed in 6 M guanidine-HCl dissolved in buffer B which contained 50 mM NaCl, 20 mM Tris-HCl (pH 8.0), 1 mM EDTA, 1 mM DTT, 10% glycerol, 1.0 mM PMSF, 10 KU/ml Trasylol, 20 μM pepstatin, and 20 μM leupeptin. Cellular debris was removed by centrifugation at 5,000 g. Supernatants were dialysed against 1.5 M guanidine-HCl hydrochloride in buffer B overnight at 4° C., then in buffer B alone for 3 hours at 4° C. Cellular debris was removed by centrifugation at 2,000 g for 15 minutes. Proteins were purified on Glutathione Sepharose-4B beads as previously described (Nasrin, et al., Nature, 354:317–320, 1991).

Electrophoretic Mobility Shift Assay (EMSA)

The EMSA procedure has been described previously (Nasrin, et al., Proc. Natl. Acad. Sci. USA, 87:5273–5277, 1990). Nuclear extract or GST-RBAP-1 was incubated with 0.25–0.5 ng of $^{32}$P-labelled oligo in 20 μl of binding buffer containing 10 mM HEPES (pH 7.9), 0.1 mM EDTA, 10 mM MgCl$_2$, 5 mM KCl, 150 mM NaCl, 25 mM DTT and 250 ng of poly(dI)poly(dC). The reaction products were separated at 4° C. in a 4.5% polyacrylamide gel run in 50 mM Tris-HCL (pH 8.5), 380 mM glycine and 2 mM EDTA. The gel was dried and exposed to film. The sequences of the oligonucleotides used to characterize IRE-A-like and E2F-like DNA binding activities are shown. Cognate E2F sites include E2F wild-type, 5'-ATTTAAGTTTCGCGC-CCTTTCTCAA-3' (SEQ ID NO: 4); E2F mutant, 5'-ATT-TAAGTTTCGATCCCTTTCTCAA-3' (SEQ ID NO: 5); DRTF wild-type, 5'-TAGTTTTCGCGCTTAAATTTGA-3' (SEQ ID NO: 6). The GAPDH IRE-A used for gel shifts included nucleotides −487 to −408 of the promoter (Nasrin, et al., Proc. Natl. Acad. Sci. USA, 87:5273–5277, 1990). For transfection analyses, the minimal binding motif 5'-AAGT-TCCCCAACTTTCCCGCCTCTCAGCCTTTGAAAG-3' (SEQ ID NO: 7) was used. In the IRE-A mutant, the central CCCGCCTC (SEQ ID NO: 8) was changed to CCCTACTC (SEQ ID NO: 3).

Methylation Interference Assay

The antisense strand from −488 to −408 of the HGAPDH promoter (IRE-A) was end-labelled with $^{32}p$ and treated with dimethyl sulfate for 4 minutes at room temperature, extracted with phenol and precipitated twice with ethanol (Gilman, et al., Mol. Cell. Biol., 6:4305–4316, 1986; Nasrin, et al., Proc. Natl. Acad. Sci. USA, 87:5273–5277, 1990). The crude nuclear extract and RBAP-1 fusion protein were incubated with 30,000 cpm of methylated probe for 1 hour at 0° C. in buffer containing 10 mM HEPES (pH 7.9), 0.1 mM EDTA, 10 mM $MgCl_2$, 5 mM KCl, 150 mM NaCl, 2.5 mM DTT, and 200 ng poly(dI)poly(dC). The mixture was separated by 5% nondenaturing polyacrylamide gel electrophoresis. Protein-bound complexes were cut from the gel and isolated by electrophoresis on a 1% agarose gel in 1 x TBE, and recovered on a DEAE membrane. The complex was eluted at 65° C. and extracted with phenol, precipitated with ethanol, and the G reaction completed with piperidine. 1,500 cpm of free or bound DNA was loaded onto an 8% sequencing gel, run in 1X TBE buffer, and subjected to autoradiography.

Western Blot Analysis

H35 hepatoma cells were grown to confluence and quiessed by incubation in serum-free medium (DMEM, 2 mM glutamine, 10 mM HEPES, 0.1% BSA) for 24 hours. Following agonist treatment, the cells were lysed in boiling SDS/urea lysis buffer (50 mM Tris pH 6.8, 2% SDS, 6 M urea, 10% glycerol, 10 mM $Na_4P_2O^7$, 100 mM NaF and 10 mM EDTA). After repeated passages of the lysate through a 19 gauge needle, protein concentrations were measured using the BCA protein assay (Pierce). DTT (100 mM) and bromophenol blue (0.01%) were added to the lysates, and each was resolved by SDS-PAGE in a 7.5% gel followed by transfer to a nitrocellulose membrane (4 hours at 400 mA) in transfer buffer (25 mM Tris, 190 mM glycine, 20% methanol). The membrane was blocked by incubation in phosphate buffered saline (PBS) containing 5% nonfat dry milk and 0.2% Tween-20 for 3 hours, then incubated for 12–16 hours with the anti-Rb antibody PMG3-245 (0.3 ug/ml) in the same buffer. The blots were probed using horseradish peroxidase conjugated goat anti-mouse IgG (BioRad), and developed using the ECL detection system (Dupont).

RESULTS

Under circumstances that lead to insulin deficiency or excess in vivo, expression of the major insulin-sensitive glucose transporter, GLUT4, is markedly regulated in epididymal fat pads (Kahn, et al., J. Clin. Invest. 84:404–411, 1989; Kahn, J. Clin. Invest. 89:1367–1374, 1992; Berger et al., Nature, 340:176–179, 1989; Sivitz, et al., Nature 340:72–74, 1989; Garvey, et al., Science, 245:60–63, 1989) in parallel with the glyceraldehyde-3-phosphate dehydrogenase (GAPDH) gene (Alexander et al., UCLA Symposia on Molecular and Cellular Biology (New York: Alan R. Liss), pp. 247–261, 1990).

Distinct Pathways Mediate Insulin's Effect on Serum-Responsive Genes and Metabolic Genes.

Figure 1A:
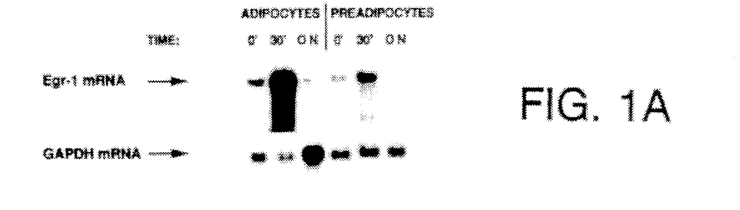

The Egr-1 gene and the glycolytic gene GAPDH show distinct patterns of response to insulin in cultured 3T3-F442A cells. In insulin-stimulated differentiated 3T3-F442A adipocytes, expression of Egr-1 increases by 30-fold (FIG. 1A). The response to insulin is rapid and transient. GAPDH mRNA levels increase 8-fold, and remain elevated as long as insulin is present (FIG. 1A; Alexander, et al., J. Biol. Chem, 260:11978–11985, 1985). Furthermore, the effect of insulin on the GAPDH gene is tissue-specific. Although insulin can stimulate Egr-1 gene expression in 3T3-F442A preadipocytes, GAPDH gene expression is not stimulated (FIG. 1A).

Figure 1B:
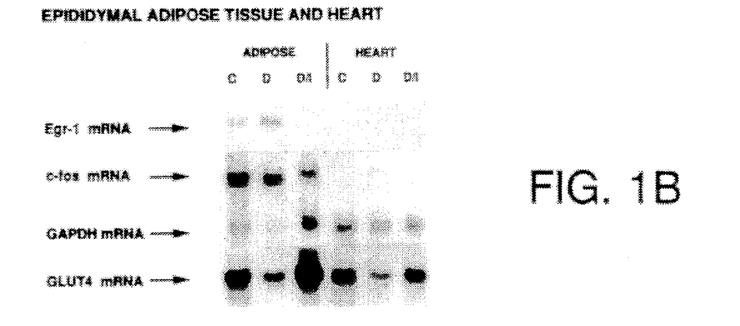

The prolonged inductive response of the GAPDH gene to insulin in the 3T3-F442A adipocyte mirrors the response of this gene to hyperinsulinemia in epididymal fat tissue in vivo. In epididymal fat pads isolated from streptozotocin-treated diabetic rats, expression of GLUT4 is reduced to 30% of normal values (Kahn, et al., J. Clin. Invest. 84:404–411, 1989; Charron et al., J. Biol. Chem., 265:7994–8000, 1990). FIG. 1B shows that GAPDH and GLUT4 are coordinately regulated during the induction of diabetes. Insulin replacement results in superinduction of GAPDH and GLUT4 mRNAs. In contrast, insulin regulation of the GAPDH and GLUT4 genes in heart is less dramatic (FIG. 1B). This tissue-specific pattern of regulation seen in cultured cells and in intact tissues is consistent with the physiologic program of insulin to increase glucose utilization in tissues that perform a specialized energy storage function in vivo.

In contrast, the effect of insulin on serum-responsive genes in cultured cells differs from the effect seen in intact tissues in vivo. Expression of the c-fos gene does not change, and the expression of Egr-1 increases in the epididymal fat pads of the diabetic animal (FIG. 1B). The expression of both genes is suppressed by prolonged insulin exposure. These results indicate that insulin is not the predominant factor regulating expression of serum-responsive genes in intact adipose tissue, and suggest that the stimulatory effect of insulin seen in cultured cells may reflect activation of a generic growth factor signalling pathway.

The observation that the effect of insulin on serum-responsive genes can be uncoupled from the pattern of insulin action on metabolic genes in tissue culture and in vivo indicates that the transient response of the Egr-1 gene and the prolonged response of the GAPDH gene to insulin reflected activation of distinct signalling pathways.

The predominant effect of insulin on Egr-1 is mediated through serum response elements (SREs) in the upstream region of the gene.

Figure 2A:
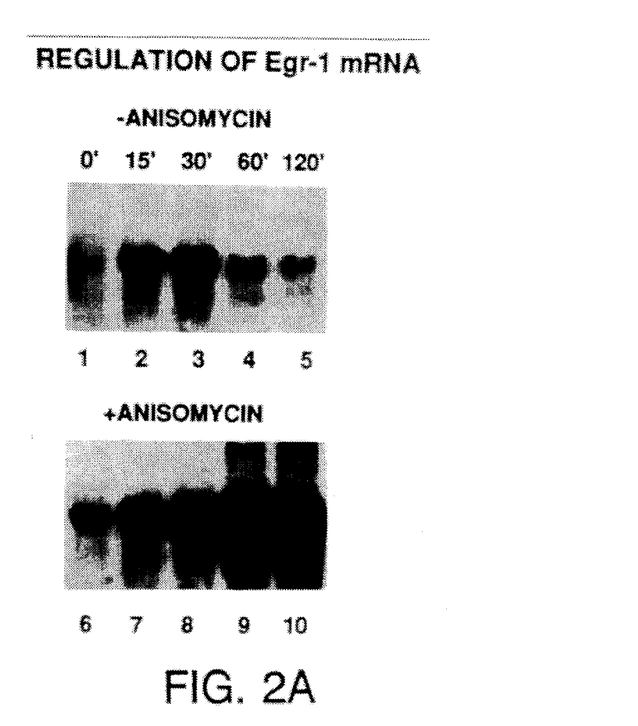
FIG. 2A is a Northern blot of RNA isolated from H35 hepatoma cells. H35 hepatoma cells were grown to confluence and serum-starved. Cells were pretreated with phosphate buffered saline or 100 μg anisomycin for 30 minutes, then exposed to 6 nM insulin for 0, 15, 30, 60, or 120 minutes. Total RNA was isolated and subjected to Northern blot analysis using an Egr-1 probe.

It has been shown that Egr-1 is an insulin-responsive gene (Sukhatme, et al., Oncogene Res., 1:343–355, 1987). In the absence of insulin, Egr-1 mRNA is barely detectable in serum-deprived H35 hepatoma cells (FIG. 2A). In the presence of insulin, Egr-1 mRNA levels increase 4-fold within 15 minutes; a maximum 14-fold stimulation is achieved within 30 minutes. In the presence of the protein synthesis inhibitor anisomycin, Egr-1 mRNA is superinduced by insulin. This pattern of induction is similar to that previously described for other serum-responsive genes such as c-fos (Greenberg, et al., Mol. Cell. Biol., 6:1050–1057, 1986; Stumpo, et al., J. Biol. Chem., 263:1611–1614, 1988).

Figure 2B:
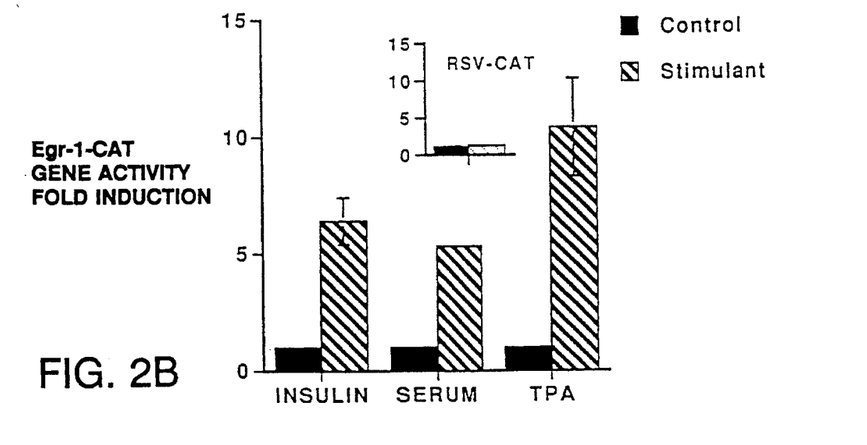
FIG. 2B is a graph showing the fold induction of Egr-1 CAT gene activity in insulin stimulated, serum stimulated, TPA-stimulated, and control H35 hepatoma cells. A fusion gene containing nucleotides −935 to +248 of the Egr-1 gene and CAT coding sequences, or the 5'-flanking sequences of the Rous Sarcoma virus (RSV) and CAT coding sequences, was cotransfected with the neomycin-resistance gene into H35 hepatoma cells, and stable lines were selected in the presence of G418. Stable lines expressing Egr-1-CAT or RSV-CAT were grown to confluence and serum-starved for 24 hours. Cells expressing Egr-1-CAT were exposed to 6 nM insulin, 15% fetal bovine serum, or 160 nM TPA for 3 hours. The half-maximal effect was achieved at an insulin concentration of 2 nM, which indicates that regulation of Egr-1 mRNA is mediated by a high affinity interaction with the insulin receptor in these cells. Insert: H35 hepatoma cells stably expressing RSV-CAT were exposed to media alone, or 6 nM insulin for 3 hours.

To confirm that the six serum response elements located in the 5'-flanking region of the Egr-1 gene (Christy et al., Mol. Cell. Biol., 9:4889–4895, 1989; Cao, et al., Mol. Cell. Biol., 10:1931–1939, 1990) can support a transcriptional response to serum and insulin, H35 hepatoma lines stably transfected with an Egr-1-CAT fusion gene (Tsai-Morris et al., Nucleic Acid Res., 16:8835–8846, 1988) containing nucleotides (–935 to +248) from the upstream region of this gene fused to CAT coding sequences were isolated. The cells were exposed to insulin (6 nM), fetal bovine serum (15%), or phorbol esters (1.6 µM) for 3 hours. The Egr-1-CAT fusion gene product was induced 6-fold by insulin or serum, and 10-fold by phorbol esters (FIG. 2B, insert). Insulin had no effect on an RSV-CAT fusion gene stably transfected, and studied in parallel (FIG. 2B, insert). These results show that Egr-1 gene expression is regulated by insulin at the transcriptional level through sequences in the 5'-flanking region of its gene.

Rapamycin Inhibits Insulin Signalling to HGAPDH-CAT, but not Egr-1-CAT.

Figure 3:
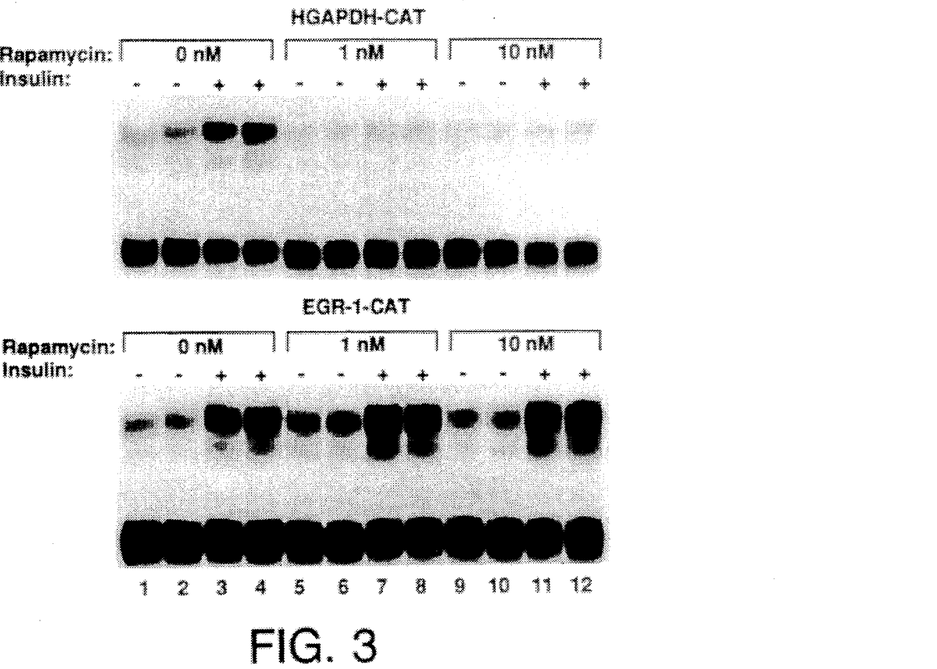

Two signalling pathways have been described for insulin based on their sensitivities to the macrolide rapamycin (Price, et al., Science, 257:973–977, 1992). The insulin receptor-linked ras-raf cascade, which culminates in sequential activation of MAP kinase and the rsk S6 kinase, is not affected by rapamycin, while an alternate insulin signalling pathway to p70 S6 kinase is inhibited by this agent. Insulin signalling to serum-responsive genes occurs through activation of the ras-raf pathway and phosphorylation of c-elk by MAP kinase (Marais, et al., Cell, 73:381–393, 1993). To determine whether the components of the insulin signal transduction pathway leading to activation of the GAPDH gene were distinct from those that activate the serum-responsive gene Egr-1, the effect of rapamycin on the transcription of these genes was examined. Cells that stably express the Egr-1-CAT gene described above, or a construct that contains a fragment (–487 to +20) of the HGAPDH gene fused to CAT, HGAPDH-CAT, were stimulated with insulin and varying concentrations of rapamycin (FIG. 3). The effect of insulin on HGAPDH-CAT activity was inhibited by as little as 1 nM rapamycin. In contrast, rapamycin did not alter the induction of Egr-1-CAT by insulin (FIG. 3). These findings indicate that distinct signalling pathways and effector proteins mediate induction of HGAPDH-CAT and Egr-1-CAT gene transcription by insulin.

Rapamycin inhibits IL-2-induced activation of p70 S6 kinase, the cyclin-dependent kinases cdk2 and cdc2, as well as cell cycle progression. Hyperphosphorylation of Rb (retinoblastoma gene product) by a cyclin-dependent kinase correlates with derepression of E2F, and reversal of the block-to-cell cycle progression from $G_1$ to S (Sherr, Cell, 73:1059–1065, 1993; Nevins, Science, 258:424–429, 1992; Hiebert, et al., Genes Dev., 6:177–185, 1992). This indicates that the distal target of insulin action through the rapamycin-sensitive pathway is E2F and its associated proteins, Rb and/or p107.

An Insulin-Responsive Element in the GAPDH Gene, IRE-A, Binds E2F-1.

Figure 4A:
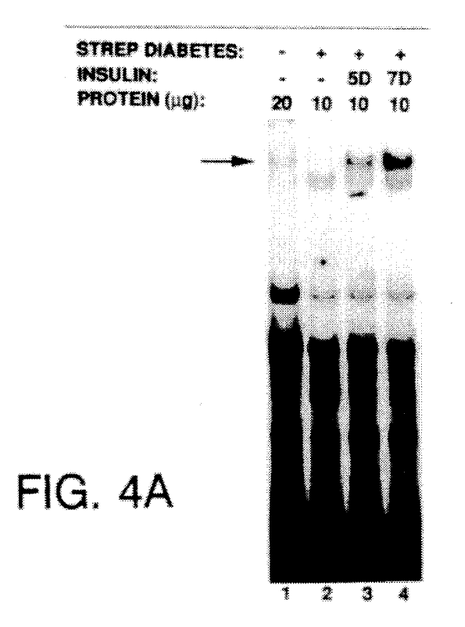
FIG. 4A is an electrophoretic mobility shift assay (EMSA) showing the regulation of IRP-A DNA binding activity in epididymal fat cells isolated from control, diabetic, and insulin-treated rats. Epididymal fat cells were isolated by collagenase treatment and nuclear proteins extracted by the method of Dignam et al. (Dignam, et al., Nucleic Acid Res., 2:1475–1489, 1983) as modified by Nasrin et al. (Nasrin, et al., Proc. Natl. Acad. Sci. USA, 87:5273–5277, 1990). Nuclear extracts were matched for extraction efficiency with an SRE from the Egr-1 gene, and incubated with 0.5 to 1 ng of $^{32}$P-labelled IRE-A-DNA in 20 μl of binding buffer containing 20 mM Hepes (pH 7.4), 150 mM NaCl, 5 mM MgCl2, 0.5 mM DTT, 0.5 mM EDTA, 20% glycerol, 0.5 mM PMSF, and 0.2 μg poly dI·dC at 4° C. for 90 minutes. Complexes were separated on an EMSA gel as described in Methods. Lane 1, control epididymal rat fat cell nuclear extract (20 μg); lane 2, streptozotocin-treated rat fat cell nuclear extract (10 μg); lane 3, streptozotocin/insulin (5-day)-treated rat fat cell nuclear extract (10 μg); lane 4, streptozotocin/insulin (7-day)-treated rat fat cell nuclear extract (10 μg).

It was previously shown that insulin regulates HGAPDH-CAT gene transcription through two cis-acting sequences, IRE-A and IRE-B (Nasrin, et al., Proc. Natl. Acad. Sci. USA, 87:5273–5277, 1990). An insulin-responsive complex, IRP-A, is detected in insulin-simulated 3T3-F442A adipocytes and the liver of carbohydrate-fed rats. Binding of the IRP-A complex to IRE-A DNA is regulated in parallel with the expression of GAPDH and GLUT4 mRNA (FIG. 1B) in epididymal fat pads isolated from diabetic rats (FIG. 4A; lanes 1 and 2) and diabetic rats treated with insulin for 5 or 7 days (FIG. 4A; lanes 3 and 4).

Figure 4B:
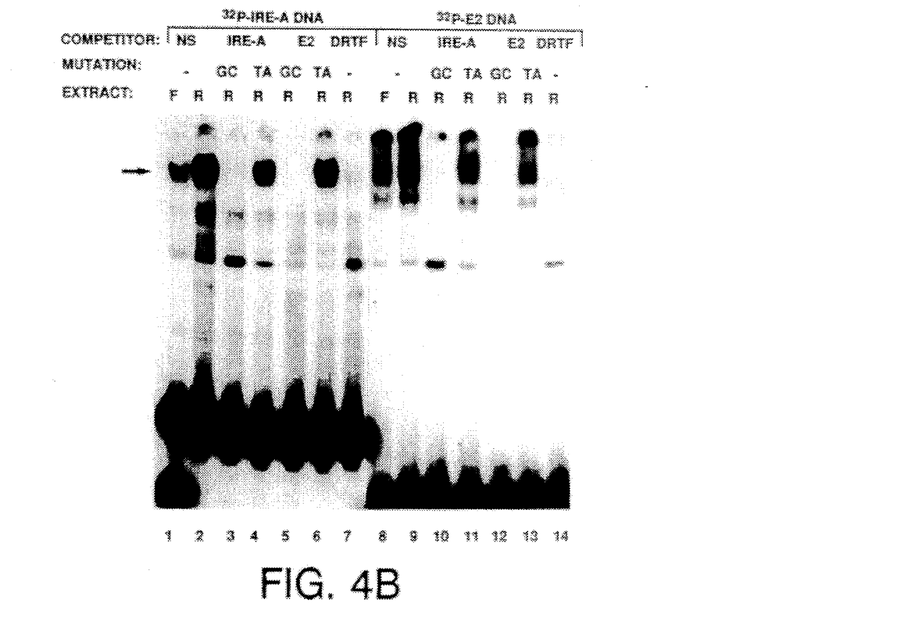
Figure 5A:
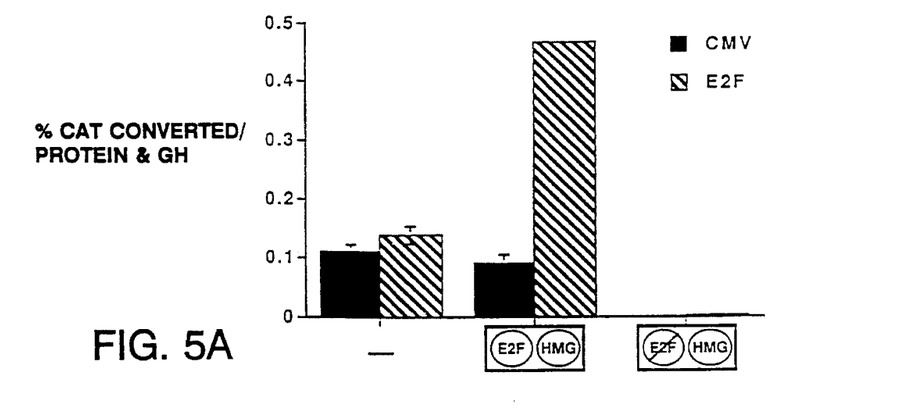
Figure 5B:
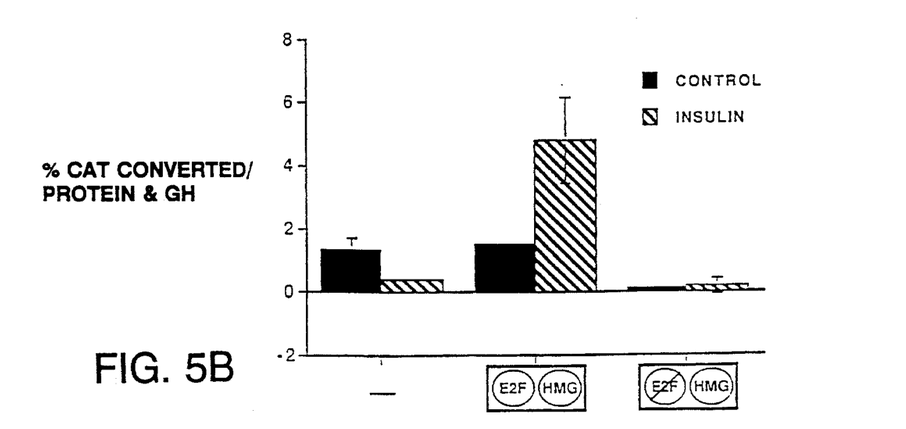
FIG. 5B is a CAT assay showing that insulin activates transcription through the IRE-A motif in H35 hepatoma cells. The HGAPDH-CAT plasmids described in FIG. 5A were used to transfect H35 hepatoma cells as described in Methods. The cells were grown to confluence, serum-starved in 0.1% crystalline BSA/DMEM, and stimulated with no agonist or 1 mU/ml insulin for 16 hours. CAT activity was corrected for protein concentration. This experiment is representative of three independent experiments.

A similar complex is also induced in the liver of animals that have been fasted then fed a high-carbohydrate, low-fat diet overnight, a manipulation that induces hyperinsulinemia in vivo (FIG. 4B; lanes 1 and 2). Mutations in the contact points between IRE-A DNA and the liver IRP-A complex inhibit binding of this complex to DNA (FIG. 4B; compare lanes 3 and 4) and the effect of insulin on IRE-A-directed gene expression in H35 hepatoma cells (Nasrin, et al., Proc. Natl. Acad. Sci USA, 87:5273–5277, 1990; FIG. 5B). These observations indicate that the regulation of IRP-A binding activity by insulin seen in intact growth-arrested lipogenic tissues in vivo is similar to that seen in terminally differentiated cells maintained in continuous culture.

A minimal DNA binding element 27 nucleotides in length, 5'-CTTTCCCGCCTCTCAGCCTTTGAAAG-3' (SEQ ID NO: 9), is required to support the formation of the IRP-A complex. The contact points between the IRP-A complex and IRE-A DNA (shown in caps), CtttCCCgCCtCt-CagC (SEQ ID NO: 10), are centered on the 5' end of this element, while the 3' end of the element carries a binding site for the SRY-like family of HMG proteins, CCTTTGAA (SEQ ID NO: 11) (Nasrin et al., Nature, 354:317–320, 1991).

To determine whether the IRP-A complex shared DNA binding specificity with E2F, two well characterized E2F/DP1 DNA binding sites were used to compete for the fasted-refed-induced liver IRP-A complex. A 50-fold excess of IRE-A DNA (FIG. 4B; lane 3) or the cognate E2 DNA binding sites found in the E2 gene (FIG. 4B; lanes 5 and 7; Helin et al., Cell, 70:337–350,1992) completely eliminated binding of the IRP-A complex to the IRE-A element. Competition of IRP-A with IRE-A DNA was eliminated when the central GC in the IRE-A DNA was mutated to TA (FIG. 4B; lane 4). Similarly, mutation of the core GC to TA in E2 DNA prevents binding of E2F to its cognate site (Helin, et al., Cell, 70:337–350, 1992; FIG. 4B; lane 13). The mutant E2 DNA also failed to compete with IRE-A DNA for the binding of the IRP-A complex (FIG. 4B; lane 6).

Interestingly, labelled E2 DNA detected a refed-induced complex of similar mobility to IRP-A (FIG. 4B; lanes 8 and 9) that showed the same pattern of competition as the IRP-A complex detected with IRE-A. (FIG. 4B; lanes 8–14). Specifically, the refed-induced E2F complex was competed by wild-type but not by mutant IRE-A DNA (FIG. 4B; lanes 10 and 11). The IRP-A E2 DNA refed-induced complexes competed with wild-type E2 DNA, and a site from the E2A promoter which binds DRTF-1 (FIG. 4B; lanes 12 and 14; Bandara et al., Nature, 351:494–497, 1991; Helin, et al., Cell, 70:337–350, 1992). Competition is not observed with mutant E2 DNA (FIG. 4B; lane 13). Thus, the proteins in the IRP-A and E2F complexes share DNA binding specificity.

Cloned RBAP-1 (E2F-1) Footprints IRE-A DNA

Figure 4C:
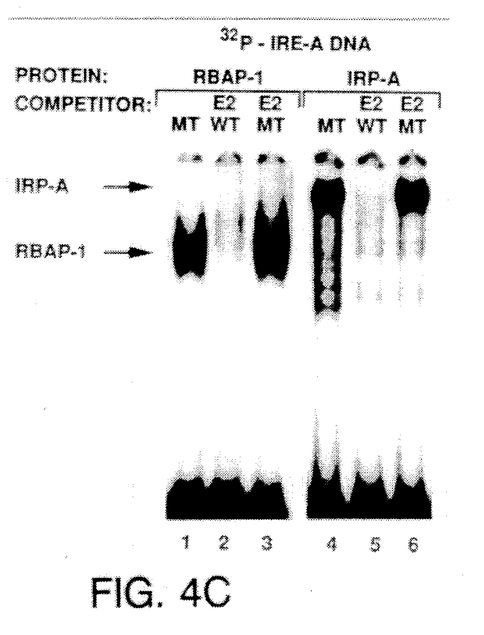
Figure 4D:
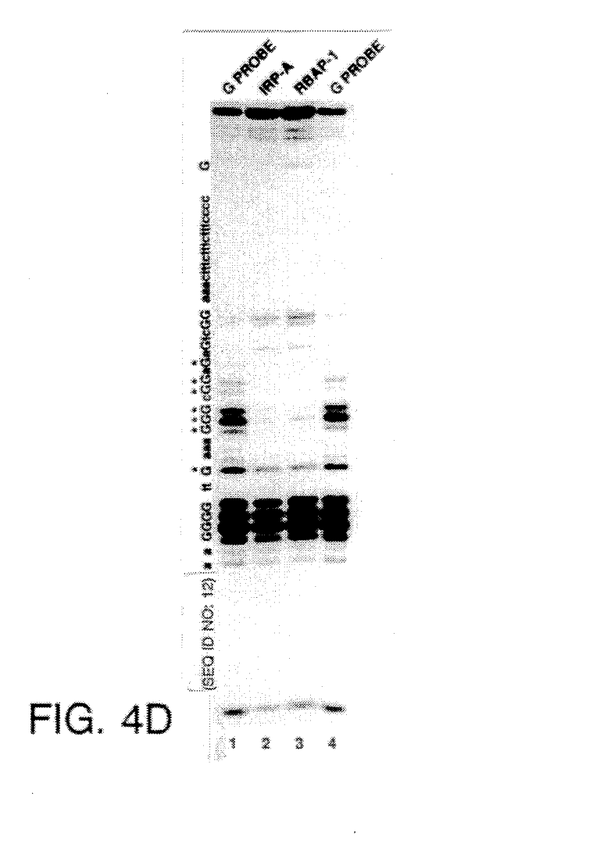

To obtain a more detailed analysis of DNA binding specificity, the contact points of the liver IRP-A complex was compared with IRE-A DNA to those obtained with the cloned Rb-associated protein RBAP-1 (E2F-1) with IRE-A DNA. Purified GST-RBAP-1, bound IRE-A DNA (FIG. 4C; lanes 1–3) and showed a similar pattern of competition with wild-type and mutant DNA sites as the IRP-A complex (FIG. 4C; lanes 4– 6). Moreover, in methylation interference assays, the contact points of the nuclear extract IRP-A complex with IRE-A DNA (FIG. 4D; lane 2) were identical to those obtained with RBAP-1 and IRE-A DNA (FIG. 4D; lane 3). Both contact the sequence CCCGCCTC (SEQ ID NO: 8). Thus, the methylation interference pattern obtained with the IRP-A complex is identical to that of RBAP-1, despite the fact that IRP-A is composed of more than one protein (Nasrin et al., Nature, 354:317–320, 1991).

E2F-1 and Insulin Stimulate IRE-A-Directed Gene Transcription.

To determine whether E2F could activate IRE-A-directed gene transcription, the effect of cloned E2F-1 on HGAPDH-CAT constructs containing −40 to +20 of the HGAPDH promoter with or without a tetramer of the minimal IRE-A DNA binding motif was examined (Nasrin et al., Proc. Natl. Acad. Sci. USA, 87:5273–5277, 1990; FIG. 5A).

In the L6 muscle cell line, the effect of E2F on the minimal promoter is negligible (FIG. 5A). In this setting, the presence of a tetramer of the wild-type IRE-A site had no effect on basal activity (FIG. 5A), while E2F-1 stimulates transcription of the IRE-A-HGAPDH-CAT construct 7-fold (FIG. 5A). The 5'-GC to TA mutation within IRE-A, which eliminates E2F DNA binding activity (FIG. 5A), markedly diminishes basal activity and E2F-1-dependent activity. This mutation does not eliminate binding of proteins to the HMG site.

The effect of insulin on these constructs was examined in the H35 hepatoma cell line (FIG. 5B). Wild-type IRE-A sites did not affect the basal activity of IRE-A-HGAPDH-CAT. Wild-type IRE-A-HGAPDH-CAT was stimulated 3fold by insulin. The 5'-(GC to TA) mutation that eliminates E2F binding, but not binding to the HMG site, reduced basal activity, and stimulated activity to background, making it difficult to assess the effect of insulin.

Insulin Activation of GAL4-E2F-1 is Blocked by Viral Oncoproteins.

To determine whether insulin stimulates E2F-1 activity independent of the DNA binding site involved, it was determined whether insulin could alter the ability of a construct encoding a GAL4 DNA binding domain, E2F-1 fusion protein GAL4-E2F-1 (Kaelin, et al., Cell, 70:351–364, 1992), to direct CAT gene expression through a tetramerized GAL4 DNA binding element (Sadowski et al., Nucleic Acid Res., 17:7539, 1989). Insulin stimulates GAL4-directed CAT expression in the presence of GAL4-E2F-1 fusion constructs that contain the entire protein GAL4-E2F-1 (1-437) (FIG. 6A) or truncated proteins that contain only the transcriptional domain of E2F-1. In this experiment, a 3 to 8 fold stimulation of GAL4-E2F-1 activity was observed in H35 hepatoma cells exposed to insulin. GAL4-E2F-1 activity is stimulated within 8 hours of insulin exposure, which indicates that the effect is not a byproduct of progression through the cell cycle.

Figure 6A:
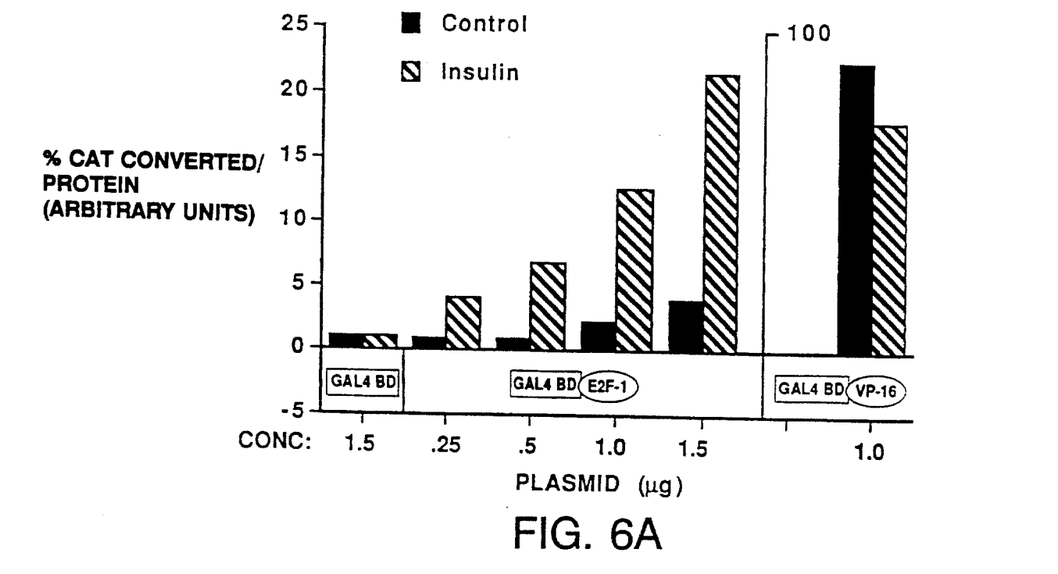
FIG. 6A is a graph showing the effect of insulin on GAL4-E2F-1, compared to the effect of insulin on GAL4-VP16. GAL4 fusion genes encoding GAL4-E2F-1 and GAL4-VP16 were cotransfected with GAL4-CAT into H35 hepatoma cells using the calcium phosphate transfection protocol described in Methods. The cells were grown to confluence and serum-starved overnight in the present or absence of insulin (1 mU/ml). CAT activity and protein concentrations were measured. The data were normalized to the CAT activity expressed by the GAL4-BD plasmid alone.

To determine whether the effect of insulin on GAL4-E 2F-1 was specific to this factor, a construct containing the transcriptionally active region of the transcription factor VP16 was analyzed. The activity of GAL4-VP-16 was not increased by insulin (FIG. 6A).

Figure 6B:
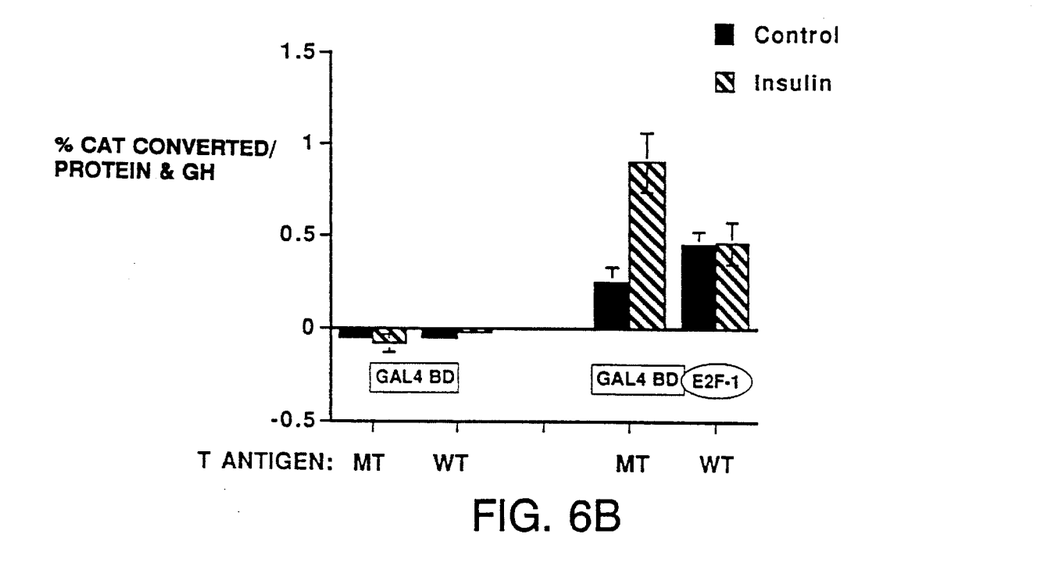
FIG. 6B is a graph showing that T antigen inhibits the effect of insulin on GAL4-E2F-1. Constructs containing the GAL4 DNA binding domain alone (GAL4 BD) or the GAL4 DNA binding domain fused to E2F-1 (GAL4 BD-E2F-1) were cotransfected with wild-type or mutant T antigen (1.5 μg/ml) and RSV-GH (1.5 μg/ml) into H35 hepatoma cells.

To determine whether basal E2F activity is inhibited by an interaction of the GAL4-E2F-1 protein with a tumor suppressor protein in H35 hepatoma cells, the effect of viral oncoproteins, which inhibit the interaction of E2F-1 with its associated proteins, on control and insulin-stimulated GAL4-E2F-1 activity was analyzed. The activity of a construct that encodes the GAL4 DNA binding domain alone was not affected by T antigen, whereas control activity of the GAL4 DNA-E2F-1 construct was increased by T antigen, and not stimulated further by insulin. This result was not observed, however, using a mutant T antigen derivative that fails to bind Rb and p107 (FIG. 6B). These observations suggest that insulin acts to derepress E2F-1.

Vital Oncoproteins that Block the Interaction between Rb and E2F-1 also Inhibit the Effect of Insulin on HGAPDH-CAT.

Figure 6C:
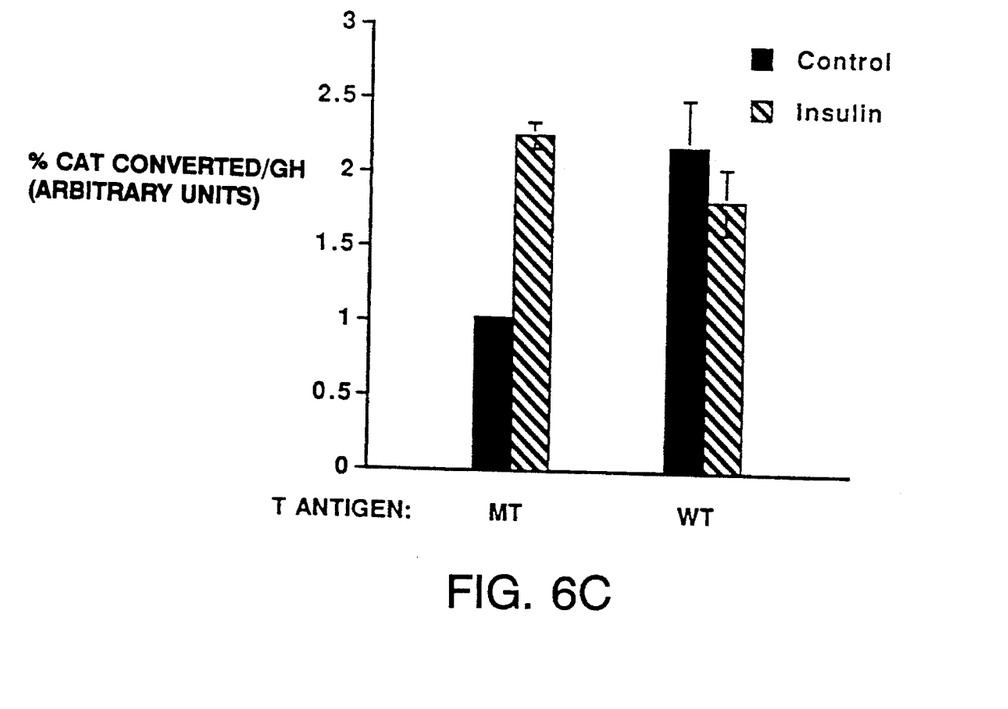

If insulin activates IRE-A-directed gene transcription by relieving the inhibitory interaction between E2F and its associated proteins, Rb or p107, disruption of this interaction by T antigen or E1A should raise basal activity of the HGAPDH-CAT construct, and inhibit the effect of insulin (FIG. 6C). In the presence of a mutant T antigen, which does not interact with Rb, the activity of the HGAPDH promoter is low, and is stimulated by insulin. In the presence of wild-type T antigen, promoter activity is derepressed and the insulin effect is abrogated. The fact that T antigen blocks the effect of insulin on GAPDH gene expression indicates that the molecular mechanism of insulin action on this gene is to derepress E2F.

Two Metabolic Genes that are Coordinately Regulated by Insulin, GAPDH and GLUT4, Carry Functional E2F-1 Sites.

To determine whether activation of E2F might be responsible for coordinate regulation of GAPDH and GLUT4 gene expression, the effect of cloned E2F-1 on the expression of HGAPDH-CAT (−487 to +21) and on a GLUT4-CAT construct (−755 to +5) was examined. Examination of the upstream region of the GLUT4 gene showed that a dimer of the CCCGCCTC (SEQ ID NO: 8) sequence was located between nucleotides −549 and −531. The effect of E2F-1 on GAPDH-CAT was 2-fold (Table 1). A similar effect (2-fold) was obtained with E2F-1 on GLUT4-CAT. Transfection of DP-1 did not stimulate GLUT4-CAT.

If the mechanism of insulin activation is derepression of E2F activity, it would be expected that T antigen derepresses GLUT4-CAT. In fact, it was observed that T antigen raises basal activity 4-fold. Moreover, in the presence of T antigen, the addition of DP-1 leads to further activation of GLUT4-CAT activity. These observations show that the GAPDH and GLUT4 promoter carry functional E2F-1 sites and imply that E2F is released by T antigen.

Insulin Promotes Hyperphosphorylation of Rb through a Rapamycin-Sensitive Cascade.

A reservoir of inactive E2F is found in association with hypophosphorylated Rb. Hyperphosphorylation of Rb results in release of an active form of the transcription factor E2F. Under physiologic circumstances, a cyclin-dependent kinase is activated in mid to late $G_1$ that phosphorylates the retinoblastoma protein. Rapamycin has been shown to block IL-2 induced activation of cdk2 and cdc2. Together these observations suggest that the ability of insulin to stimulate a rapamycin-sensitive Rb kinase might be the proximal step in activation of an E2F (or a partner that interacts with E2F) in H35 hepatoma cell lines.

To determine whether hyperphosphorylation of Rb is the rapamycin-sensitive step in insulin action on GAPDH gene transcription, the effect of insulin on Rb hyperphosphorylation in the presence and absence of rapamycin was examined. The ability of growth factors and serum to stimulate Rb hyperphosphorylation can be detected by Western blot analysis due to the marked alteration in migration of the protein seen on SDS-PAGE when Rb is phosphorylated at amino acids 800 and 804 by cyclin-dependent kinases (Hamel et al., Mol. Cell. Biol., 12:3431–3438, 1992).

Figure 7:
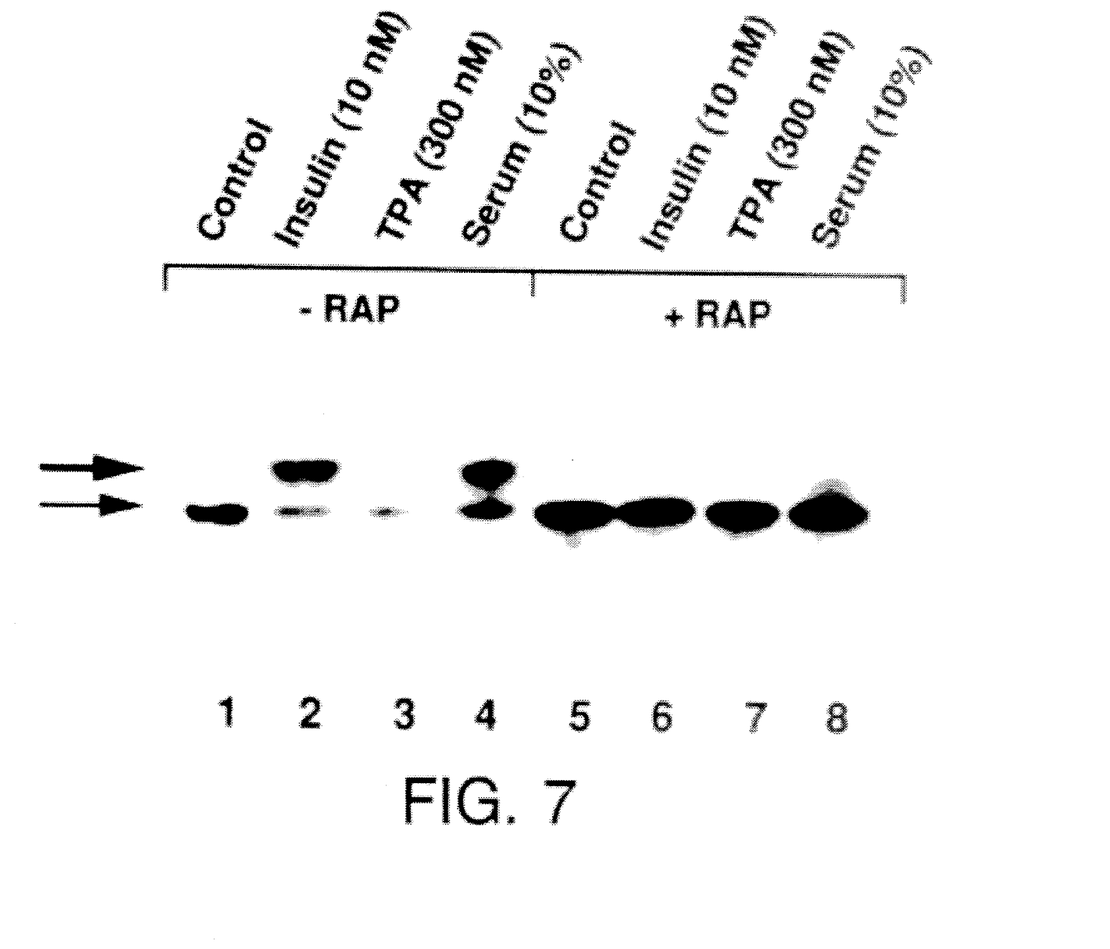

The phosphorylation state of Rb in control cells grown in bovine serum albumin was compared to that in cells stimulated with insulin or 15% serum (FIG. 7). The mobility of Rb is markedly shifted in insulin-stimulated cells, indicating that Rb is hyperphosphorylated by insulin (FIG. 7; lanes 1 and 2). The effect of insulin on Rb hyperphosphorylation is equivalent to that of serum (FIG. 7; lanes 2 and 4). Rapamycin inhibits the effect of insulin and serum on Rb hyperphosphorylation, indicating that the pathways utilized by insulin and serum are similar (FIG. 7; lanes 5–8). Phorbol esters stimulate MAP kinase and Egr-1CAT activity in these cells (FIG. 2B) but not hyperphosphorylation of Rb (FIG. 7; lanes 1 and 3). These results suggest that insulin signalling through the rapamycin-sensitive signalling cascade activates a cyclin-dependent kinase(s) that underlies the phosphorylation of Rb and possibly other tumor-suppressor genes.

Table 1. Fold Effect of E2F, DP1, and T Antigen on GLUT4-CAT Activity.

Segments of the GLUT4 promoter (–2.3 kb, or –755 to +5) were fused to CAT. These plasmids (15/mg/ml) were cotransfected with RSV-β galactosidase (7 μg/ml) and CMV (50 ng) or CMV-E2F (50 ng) into Chinese hamster ovary (CHO) cells using the calcium phosphate transfection procedure described in Methods, except that the cells were shocked with 10% glycerol/PBS for 1 minute. Cells were serum-starved in 0.1% BSA/DMEM, and then harvested for CAT activity analysis as described in Methods.

TABLE 1

Fold Effect of E2F, DP1, and T Antigen on GLUT4-CAT Activity

| FACTOR | CAT/βGAL | F.E. |
|---|---|---|
| GLUT4-CAT | | |
| –T Antigen | | |
| CMV | 2.0 ± 0.3 | 1.0 |
| DP1 | 2.0 ± 0.3 | 1.0 |
| E2F | 3.3 ± 0.7 | 1.6 |
| E2F + DP1 | 4.0 ± 0.5 | 2.0 |
| +T Antigen | | |
| CMV | 9.1 ± 1.2 | 1.0 |
| DP1 | 16.0 ± 0.8 | 1.8 |
| E2F | 12.6 ± 1.9 | 1.4 |
| E2F + DP1 | 13.7 ± 0.8 | 1.5 |
| GAPDH-CAT | | |
| –T Antigen | | |
| CMV | 2.6 ± 0.4 | 1.0 |
| E2F | 5.2 ± 1.4 | 2.0 |

Other Embodiments

From the above description, one skilled in the art can easily ascertain the essential characteristics of the present invention, and without departing from the spirit and scope thereof, can make various changes and modifications of the invention to adapt it to various usages and conditions.

All publications cited herein are fully incorporated by reference in their entirety. Other embodiments are in the claims set forth below.

What is claimed is:

1. A method of treating obesity caused by hyperinsulinemia, said method comprising the steps of:
   (a) identifying an adult in need of such treatment; and
   (b) administering to said adult an amount of rapamycin effective to inhibit insulin-induction of GAPDH, acetyl CoA carboxylase, or GLUT4 gene expression in said adult.

2. The method of claim 1, wherein said adult has or is at risk of developing type II diabetes.

3. The method of claim 1, wherein said administering is enteral, parenteral, or transmucosal, or by inhalation or implant.

4. A method of inhibiting weight gain, said method comprising the steps of:
   (a) identifying a patient who is in need of prevention of weight gain resulting from hyperinsulinemia; and
   (b) administering to said patient an amount of rapamycin effective to reduce said weight gain.

5. The method of claim 4, wherein said hyperinsulinemia is attributable to insulin administered to said patient.

6. The method of claim 4, wherein said hyperinsulinemia is attributable to abnormally high levels of endogenous insulin in said patient.

7. The method of claim 4, wherein said administering is enteral, parenteral, or transmucosal, or by inhalation or implant.

8. A method of treating complications of hyperinsulinemia, said method comprising the steps of:
   (a) identifying a patient in need of such treatment; and
   (b) administering to said patient an amount of rapamycin effective to inhibit insulin-induction of GAPDH, acetyl CoA carboxylase, or GLUT4 gene expression in said patient.

9. The method of claim 8, wherein said administering is enteral, parenteral, or transmucosal, or by inhalation or implant.

10. A method of inhibiting an insulin-stimulated increase in fat content in a cell, said method comprising contacting said cell with an amount of rapamycin effective to inhibit induction of GAPDH, acetyl CoA carboxylase, or GLUT4 gene expression in said cell.

11. The method of claim 10, wherein said cell is an adipocyte.

12. The method of claim 10, wherein said cell is an hepatocyte.

13. The method of claim 10, wherein said cell is in an animal.

14. The method of claim 13, wherein said animal is a mammal.

15. The method of claim 14, wherein said mammal is a human.

16. The method of claim 13, wherein said animal has or is at risk of developing hyperinsulinemia.

17. The method of claim 13, wherein said animal has or is at risk of developing type II diabetes.

18. The method of claim 13, wherein said animal has or is at risk of developing obesity.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
      ( A ) LENGTH: 12
      ( B ) TYPE: nucleic acid
      ( C ) STRANDEDNESS: single
      ( D ) TOPOLOGY: linear    ( x i ) SEQUENCE DESCRIPTION: SEQ ID NO: 1:

GAGGCGGGAA AG         12

( 2 ) INFORMATION FOR SEQ ID NO: 2:

( i ) SEQUENCE CHARACTERISTICS:
      ( A ) LENGTH: 11
      ( B ) TYPE: nucleic acid
      ( C ) STRANDEDNESS: single
      ( D ) TOPOLOGY: linear    ( x i ) SEQUENCE DESCRIPTION: SEQ ID NO: 2:

TTTCCCGCCT C         11

( 2 ) INFORMATION FOR SEQ ID NO: 3:

( i ) SEQUENCE CHARACTERISTICS:
      ( A ) LENGTH: 8
      ( B ) TYPE: nucleic acid
      ( C ) STRANDEDNESS: single
      ( D ) TOPOLOGY: linear    ( x i ) SEQUENCE DESCRIPTION: SEQ ID NO: 3:

CCCTACTC 8

(2) INFORMATION FOR SEQ ID NO: 4:

(i) SEQUENCE CHARACTERISTICS:
        (A) LENGTH: 25
        (B) TYPE: nucleic acid
        (C) STRANDEDNESS: single
        (D) TOPOLOGY: linear     (xi) SEQUENCE DESCRIPTION: SEQ ID NO: 4:

ATTTAAGTTT CGCGCCCTTT CTCAA 25

(2) INFORMATION FOR SEQ ID NO: 5:

(i) SEQUENCE CHARACTERISTICS:
        (A) LENGTH: 25
        (B) TYPE: nucleic acid
        (C) STRANDEDNESS: single
        (D) TOPOLOGY: linear     (xi) SEQUENCE DESCRIPTION: SEQ ID NO: 5:

ATTTAAGTTT CGATCCCTTT CTCAA 25

(2) INFORMATION FOR SEQ ID NO: 6:

(i) SEQUENCE CHARACTERISTICS:
        (A) LENGTH: 22
        (B) TYPE: nucleic acid
        (C) STRANDEDNESS: single
        (D) TOPOLOGY: linear     (xi) SEQUENCE DESCRIPTION: SEQ ID NO: 6:

TAGTTTTCGC GCTTAAATTT GA 22

(2) INFORMATION FOR SEQ ID NO: 7:

(i) SEQUENCE CHARACTERISTICS:
        (A) LENGTH: 37
        (B) TYPE: nucleic acid
        (C) STRANDEDNESS: single
        (D) TOPOLOGY: linear     (xi) SEQUENCE DESCRIPTION: SEQ ID NO: 7:

AAGTTCCCCA ACTTTCCGC CTCTCAGCCT TTGAAAG 37

(2) INFORMATION FOR SEQ ID NO: 8:

(i) SEQUENCE CHARACTERISTICS:
        (A) LENGTH: 8
        (B) TYPE: nucleic acid
        (C) STRANDEDNESS: single
        (D) TOPOLOGY: linear     (xi) SEQUENCE DESCRIPTION: SEQ ID NO: 8:

CCCGCCTC 8

(2) INFORMATION FOR SEQ ID NO: 9:

(i) SEQUENCE CHARACTERISTICS:
        (A) LENGTH: 26
        (B) TYPE: nucleic acid
        (C) STRANDEDNESS: single
        (D) TOPOLOGY: linear     (xi) SEQUENCE DESCRIPTION: SEQ ID NO: 9:

CTTTCCCGCC TCTCAGCCTT TGAAAG 26

( 2 ) INFORMATION FOR SEQ ID NO: 10:

( i ) SEQUENCE CHARACTERISTICS:
( A ) LENGTH: 17
( B ) TYPE: nucleic acid
( C ) STRANDEDNESS: single
( D ) TOPOLOGY: linear ( x i ) SEQUENCE DESCRIPTION: SEQ ID NO: 10:

CTTTCCCGCC TCTCAGC 17

( 2 ) INFORMATION FOR SEQ ID NO: 11:

( i ) SEQUENCE CHARACTERISTICS:
( A ) LENGTH: 8
( B ) TYPE: nucleic acid
( C ) STRANDEDNESS: single
( D ) TOPOLOGY: linear ( x i ) SEQUENCE DESCRIPTION: SEQ ID NO: 11:

CCTTTGAA 8

( 2 ) INFORMATION FOR SEQ ID NO: 12:

( i ) SEQUENCE CHARACTERISTICS:
( A ) LENGTH: 46
( B ) TYPE: nucleic acid
( C ) STRANDEDNESS: single
( D ) TOPOLOGY: linear ( x i ) SEQUENCE DESCRIPTION: SEQ ID NO: 12:

AAGGGGTTGA AAGGGCGGAG AGTCGGAAAC TTTCTTTCTT TCCCCG 46